United States Patent [19]

Fabre et al.

[11] Patent Number: 4,584,297
[45] Date of Patent: Apr. 22, 1986

[54] PYRROLO[1,2-C]-1,3-THIAZINES

[75] Inventors: Jean-Louis Fabre, Paris; Daniel Farge, Thiais; Claude James; Daniel Lave, both of Paris, all of France

[73] Assignee: Rhone-Poulenc Sante, Courbevoie, France

[21] Appl. No.: 721,773

[22] Filed: Apr. 10, 1985

Related U.S. Application Data

[62] Division of Ser. No. 569,907, Jan. 11, 1984, Pat. No. 4,546,100.

[30] Foreign Application Priority Data

Jan. 13, 1983 [FR] France .................. 83 00454

[51] Int. Cl.$^4$ ............... C07D 417/14; A61K 31/54
[52] U.S. Cl. ............................. 514/226; 514/222; 544/3; 544/47
[58] Field of Search ............ 544/47, 3; 514/226, 514/222

[56] References Cited

U.S. PATENT DOCUMENTS 3,294,539  12/1966  Bailey ........................ 96/84

FOREIGN PATENT DOCUMENTS 1401707  4/1965  France .
1069243  6/1967  United Kingdom .

Primary Examiner—John M. Ford
Attorney, Agent, or Firm—Stevens, Davis, Miller & Mosher

[57] ABSTRACT

Antithrombotics of the formula

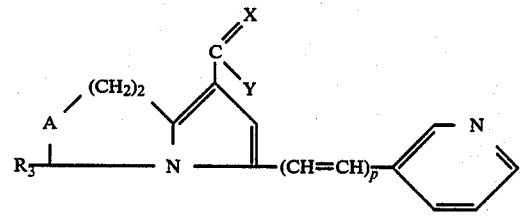

in which $A = S$, $SO$ or $SO_2$, $R_3 = H$, alkyl or substituted or unsubstituted phenyl, $X = O$, $S$, $NH$ or variously substituted nitrogen, p is 0 or 1 and $y = H$, $NH_2$, or various substituted amines.

6 Claims, No Drawings

PYRROLO[1,2-C]-1,3-THIAZINES

This is a division of application Ser. No. 569,907 filed Jan. 11, 1984, now U.S. Pat. No. 4,546,100.

The present invention provides new heterocyclic compounds of the formula:

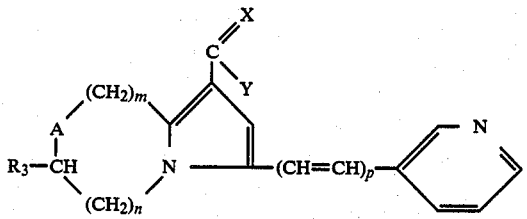

in which m represents 1 or 2 and n 0, 1 or 2, the sum of m+n being 1, 2 or 3, A represents sulphur, oxygen, methylene, sulphinyl or sulphonyl, $R_3$ represents hydrogen, alkyl, or phenyl (unsubstituted or substituted by halogen, alkyl, alkoxy or trifluoromethyl); and (a) X represents oxygen or sulphur or an imino or hydroxyimino radical, P represents 0 or 1 and Y represents a radical of the formula:

in which $R_1$ and $R_2$ both represent hydrogen, or $R_1$ represents hydrogen and $R_2$ represents hydroxyl or alkyl of 1 to 5 carbon atoms, which is substituted by a carboxyl, amino, alkylamino, dialkylamino, hydroxyalkylamino, morpholino or imidazolyl radical, a piperazin-1-yl radical [unsubstituted or substituted in the 4-position by alkyl, benzyl (optionally substituted by a halogen, alkyl, alkoxy or trifluoromethyl) or a phenyl radical (optionally substituted by halogen, alkyl, alkoxy or trifluoromethyl)] or a piperidino or pyrrolidin-1-yl radical, or alternatively $R_2$ represents a phenyl radical substituted by one or more hydroxyl, carboxyl, amino, alkylamino or dialkylamino radicals, or alternatively $R_1$ and $R_2$ form, with the nitrogen atom to which they are bonded, a 5-membered or 6-membered ring which can also contain another heteroatom such as oxygen, sulphur or nitrogen, and which is unsubstituted or substituted by alkyl, alkoxycarbonyl, hydroxyalkyl, aminoalkyl, alkylaminoalkyl or dialkylaminoalkyl, benzyl (optionally substituted by halogen, alkyl, alkoxy, trifluoromethyl) or a pyrrolidin-1-yl-carbonylalkyl radical, or (b) X represents dialkylhydrazono, Y represents amino and p represents 0 or 1, or (c) X and Y form with the carbon atom to which they are bonded a δ2-thiazolin-2-ylδ or 2-imidazolin-2-yl radical, and p represents 0 or 1, or (d) X represents oxygen, Y represents hydrogen and p is 0, the aforesaid alkyl radicals and alkyl portions of other radicals (and the alkyl radicals and alkyl portions mentioned hereinafter) being straight-chain or branched-chain and containing, unless otherwise stated, 1 to 4 carbon atoms, and including the tautomeric forms of the said compounds where X represents imino, hydroxyimino or dialkylhydrazono and Y represents a radical of the formula (II) in which $R_1$ represents a hydrogen atom, or where X represents oxygen or sulphur and Y represents a radical of the formula (II) in which $R_1$ represents a hydrogen atom and $R_2$ represents a hydroxyl radical; and their acid addition salts and, where they exist, salts with metals and nitrogen-containing bases.

According to a feature of the invention, the compounds of the formula (I) in which m, n, A and $R_3$ are defined as above and the other symbols are defined as above under (a), except that X cannot represent a sulphur atom or an imino or hydroxyimino radical, are prepared by reacting ammonia or an amine of the formula:

in which $R_1$ and $R_2$ are defined as above under (a), with an acid of the formula:

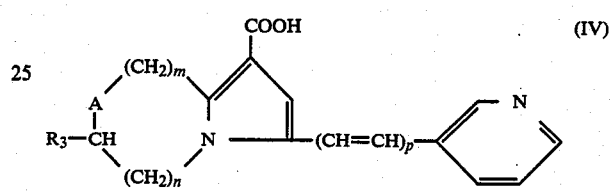

in which the various symbols are defined as above.

It is particularly advantageous to use the acid of the general formula (IV) in an activated form, such as the acid chloride, or to react it with N,N'-carbonyldiimidazole or an alkyl chloroformate before reaction with ammonia or the amine of the general formula (III).

It is generally preferable to react the acid chloride and to carry out the reaction in an organic solvent such as chloroform or methylene chloride, at a temperature of between 0° C. and the reflux temperature of the reaction mixture.

The acids of the general formula (IV) can be prepared by hydrolysing the nitriles of the general formula:

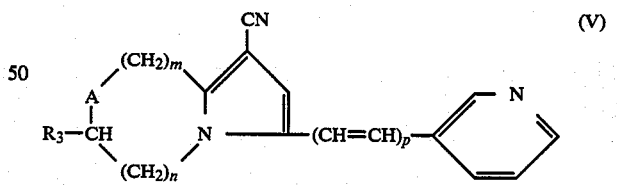

in which m, n, A and $R_3$ are defined as above and p is defined as above under (a), by any method known to those skilled in the art for converting a nitrile to an acid without affecting the rest of the molecule. It is generally advantageous to carry out the hydrolysis in a basic medium in an alcohol of high b.p., e.g. by means of potassium hydroxide in ethylene glycol, at between 100° C. and the reflux temperature of the reaction mixture.

The nitriles of the general formula (V) can be obtained by reacting 2-chloroacrylonitrile of the formula:

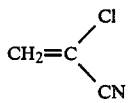

with a product of the general formula:

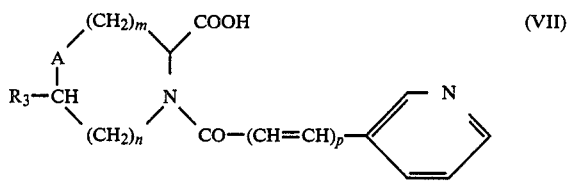

in which the various symbols have the corresponding definitions.

The reaction is generally carried out in acetic anhydride by heating to a temperature of between 80° and 130° C.

The products of the general formula (VII) can be obtained by condensing a product of the general formula:

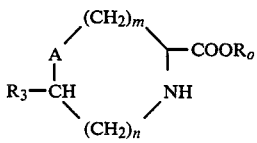

in which p is equal to 0 or 1 and $Z_o$ represents an acid-activating group such as a halogen atom, with a product of the general formula:

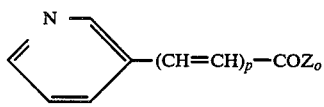

in which $R_o$ represents a hydrogen atom or an alkyl radical, this being followed by hydrolysis in the case where $R_o$ represents an alkyl radical.

The condensation of the product of the general formula (VIII) with the product of the general formula (IX) is generally carried out in an inert organic solvent such as chloroform, in the presence of an acid acceptor such as triethylamine, at a temperature of between 0° and 65° C.

If $R_o$ represents an alkyl radical, the hydrolysis is carried out by any method known to those skilled in the art for converting an ester to an acid without affecting the rest of the molecule, in particular by treatment in an alkaline medium in water or an aqueous-alcoholic solvent such as a water/ethanol mixture, at a temperature of between 20° and 80° C.

The products of the general formula (IX) can be obtained by application or adaptation of the methods described by H. T. NAGASAWA, J. A. ELBERLING, P. S. FRASER and N. S. NIZUNO, J. Med. Chem. 14, 501 (1971), B. BELLEAU, J. Med. Chem 2, 553 (1960), J. C. WRISTON and C. G. McKENZIE, J. Biol. Chem., 225, 607 (1957), S. WOLFF, G. MILITELLO et al., Tet. Letters, 3913 (1979), H. GERSHON and A. SCALA, J. Org. Chem. 26, 2347, (1961), R. RIEMSCHNEIDER and G. A. HOYER, Z. Naturforsch. 17 B, 765 (1962), H. MOHRLE and C. KARL, Arch. Pharm. 301, 728 (1968), or R. K. HILL, T. H. CHAN, and J. A. JOULE, Tetrahedron 21, 147 (1965).

If A represents an oxygen atom and n is equal to 0, the product of the general formula (IX) is not isolated but the product of the general formula (VII) is obtained directly, the condensation of the product of the general formula (VIII) being carried out in situ in the reaction mixture.

According to the invention, the products of the general formula (I) in which m, n, A and $R_3$ are defined as above, p is equal to 0 or 1, X represents an oxygen atom and Y represents a radical of the general formula (II) in which $R_1$ and $R_2$ both represent a hydrogen atom can also be prepared directly by hydrolysing the nitrile of the general formula (V).

The hydrolysis can be carried out by any means known to those skilled in the art for converting a nitrile to an amide without affecting the rest of the molecule, in particular by heating in an alkaline medium in an organic solvent such as tert.butanol, at a temperature of between 30° and 85° C.

According to the invention, the products of the general formula (I) in which m, n, A and $R_3$ are defined as above, p is equal to 0 or 1, X represents an oxygen atom and Y represents a radical of the general formula (II) in which $R_1$ and $R_2$ both represent a hydrogen atom can also be prepared by condensing 2-chloroacrylamide of the formula:

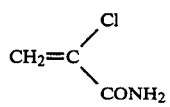

with an acid of the general formula (VII).

The reaction is generally carried out in acetic anhydride by heating to a temperature of between 80° and 130° C.

According to the invention, the products of the general formula (I) in which m, n, A and $R_3$ are defined as above, p is equal to 0 or 1, X represents a sulphur atom and Y is defined as above under (a), except that it cannot represent a radical of the general formula (II) in which $R_1$ represents a hydrogen atom and $R_2$ represents a hydroxyl radical, can be prepared by thionating a product of the general formula (I) in which X represents an oxygen atom and the other symbols have the corresponding meanings, i.e. a product of the general formula:

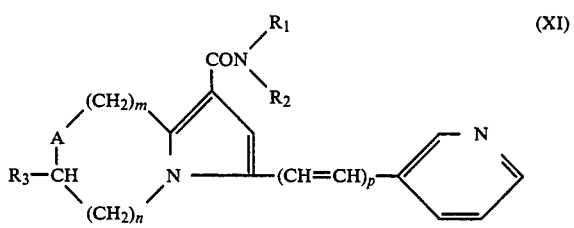

The reaction is generally carried out by means of a thionating reagent such as phosphorus pentasulphide, in an organic solvent such as toluene, dioxane or pyridine, at a temperature of the order of 100° C., or by means of LAWESSON's reagent [2,4-bis-(4-methoxyphenyl)-1,3,2,4-dithiadiphosphetane-2,4-dithione], in an organic solvent such as toluene, at a temperature of the order of 50° C., or such as 1,2-dimethoxyethane or hexamethylphosphoramide, at a temperature of the order of 20° C.

According to the invention, the products of the general formula (I) in which m, n, A and $R_3$ are defined as above, X represents a hydroxyimino radical and Y and p are defined as above under (a) can be prepared by reacting hydroxylamine with a product of the general formula (I) in which m, n, A and $R_3$ are defined as above, X represents a sulphur atom and Y and p are defined as above under (a), i.e. with a product of the general formula:

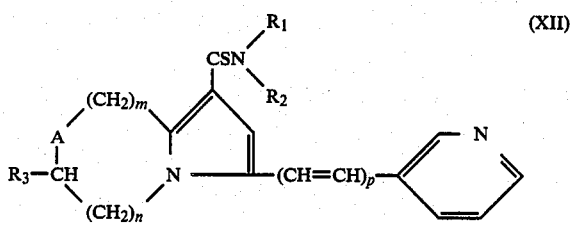

in which the various symbols have the corresponding definitions.

Hydroxylamine hydrochloride is generally used and the reaction is carried out in the presence of mercuric chloride, in pyridine or in an organic solvent such as ethanol or methanol, in the presence of an acid acceptor such as triethylamine, at a temperature of between 20° and 80° C.

According to the invention, the products of the general formula (I) in which m, n, A and $R_3$ are defined as above, X represents an imino radical and Y and p are defined as above under (a) can be prepared by reacting ammonia or an amine of the general formula (III) in which $R_1$ and $R_2$ are defined as above, with an iminothioether of the general formula:

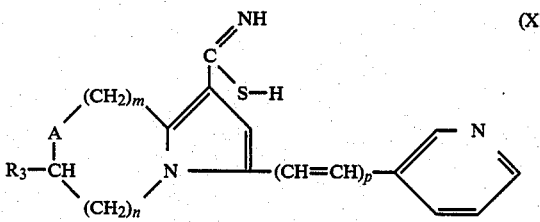

in which R represents an alkyl radical, preferably methyl, m, n, A and $R_3$ are defined as above and p is defined as above under (a).

The reaction is generally carried out in an organic solvent such as chloroform, in the presence of a weak acid such as acetic acid, at a temperature of between 20° and 65° C.

The iminothioether of the general formula (XIII) can be prepared by reacting an alkyl halide of the general formula:

R—Z  (XIV)

in which R is defined as above and Z represents a halogen atom, preferably an iodine atom, with a product of the general formula (I) in which m, n, A and $R_3$ are defined as above, p is equal to 0 or 1, X represents a sulphur atom and Y represents a radical of the general formula (II) in which $R_1$ and $R_2$ both represent a hydrogen atom, i.e. a product of the general formula:

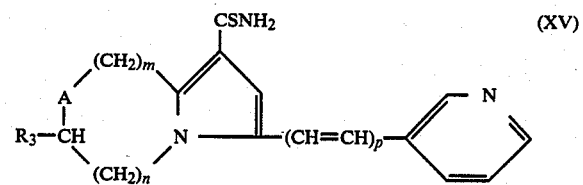

in which the various symbols have the corresponding definitions.

The reaction is generally carried out in an organic solvent such as acetone or a mixture of acetone and dimethylformamide, at a temperature of between 0° and 50° C.

According to the invention, the products of the general formula (I) in which m, n, A and $R_3$ are defined as above, X represents a sulphur atom, Y represents a radical of the general formula (II) in which $R_1$ and $R_2$ both represent a hydrogen atom and p is equal to 0, i.e. a product of the general formula (XV) in which the symbols have the corresponding definitions, can be prepared from the nitriles of the general formula (V) by any method known to those skilled in the art for converting a nitrile to a thioamide without affecting the rest of the molecule. It is particularly advantageous to react hydrogen sulphide with the nitrile of the general formula (V), in a solvent such as pyridine, in the presence of triethylamine, at a temperature of between 0° and 50° C.

According to the invention, the products of the general formula (I) in which m, n, a and $R_3$ are defined as above and X, Y and p are defined as above under (b) can be prepared by reacting a dialkylhydrazine of the general formula:

in which R' and R" represent identical or different alkyl radicals, with an iminothioether of the general formula (XIII) in which the symbols have the corresponding definitions.

The reaction is generally carried out in an organic solvent such as ethanol, at a temperature of between 20° and 80° C.

According to the invention, the products of the general formula (I) in which m, n, A and $R_3$ are defined as above, p is equal to 0 or 1, X represents an oxygen atom and Y represents a radical of the general formula (II) in which $R_1$ represents a hydrogen atom and $R_2$ represents an alkyl radical containing 1 to 5 carbon atoms, which is substituted by a hydroxyalkylamino radical, it being understood tht the alkyl radical and the alkyl portion of the hydroxyalkylamino radical contain the same number of carbon atoms, can also be prepared by reacting an amino alcohol of the general formula:

$H_2N$—Q—OH 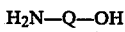 (XVII)

in which Q represents an alkylene radical containing 1 to 5 carbon atoms, with a nitrile of the general formula (V).

The reaction is generally carried out in an excess of aminoalcohol of the general formula (XVII), in the presence of lithium chloride and at a temperature of between 100° C. and the reflux temperature of the reaction mixture.

According to the invention, the products of the general formula (I) in which m, n, A and $R_3$ are defined as above and X, Y and p are defined as above under (c) can be prepared by reacting a product of the general formula:

$$H_2NCH_2CH_2-T-H \qquad (XVIII)$$

in which T represents a sulphur atom or an imino radical, with a nitrile of the general formula (V).

The reaction is generally carried out in an organic solvent such as an alcohol, or in an excess of the products of the general formula (XVIII), at a temperature of between 60° C. and the reflux temperature of the reaction mixture.

According to the invention, the products of the general formula (I) in which m, n, A and $R_3$ are defined as above, X and Y form a $\Delta^2$-imidazolinyl radical with the carbon atom to which they are bonded and p is equal to 0 can also be prepared by reacting ethylenediamine with a dithioester of the general formula:

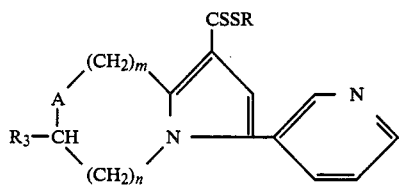
(XIX)

in which R represents an alkyl radical and the other symbols are defined as above.

The reaction is generally carried out in an excess of ethylenediamine, in the presence of mercuric chloride, at a temperature of between 60° C. and the reflux temperature of the reaction mixture.

The dithioesters of the general formula (XIX) can be prepared by reacting hydrogen sulphide with a product of the general formula (XIII) in which the symbols have the corresponding definitions.

The reaction is generally carried out in a solvent such as pyridine, at a temperature of the order of 20° C.

According to the invention, the products of the general formula (I) in which m, n, A and $R_3$ are defined as above and X, Y and p are defined as above under (d) can be prepared by formylating a product of the general formula:

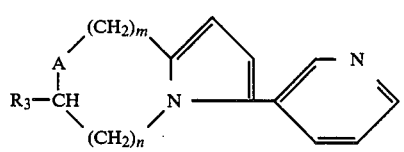
(XX)

in which the symbols are defined as above.

The formylation is generally carried out by any means known to those skilled in the art for formylating a pyrrole nucleus without affecting the rest of the molecule, in particular by means of a mixture of phosphoryl chloride and dimethylformamide, at a temperature of between 0° C. and 20° C.

The products of the general formula (XX) can be prepared by decarboxylating an acid of the general formula (IV) in which p is equal to 0 and the other symbols are defined as above, by the methods which are in themselves known for decarboxylating an acid, e.g. by heating in the presence of copper powder.

According to the invention, the products of the general formula (I) in which A represents a sulphinyl or sulphonyl radical and the other symbols are defined as above, except that X cannot represent a sulphur atom and p cannot be equal to 1, can be prepared by oxidising a product of the general formula (I) in which A represents a sulphur atom and the other symbols are defined as above, i.e. a product of the general formula:

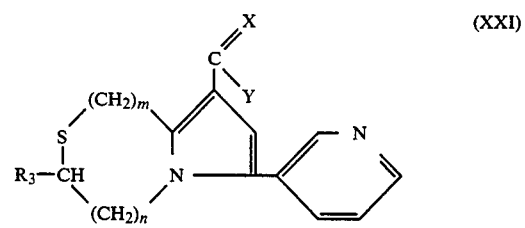
(XXI)

by any means known to those skilled in the art for converting a sulphide to a sulphoxide or a sulphone without affecting the rest of the molecule.

The oxidation can be carried out e.g. by employing a reagent commonly used for converting a sulphide to a sulphoxide or a sulphone, the reaction being carried out in a suitable solvent. By way of example, it is possible to use hydrogen peroxide in acetone or acetic acid, an alkali metal periodate in an alcohol or acetonitrile, or a percarboxylic acid (peracetic, perbenzoic, m-chloroperbenzoic, p-nitroperbenzoic or perphthalic acid) in an ether (dioxane, tetrahydrofuran or diethyl ether), a chlorinated solvent (methylene chloride or dichloroethane), acetic acid or a mixture of these solvents. The reaction is generally carried out at a temperature of between −10° and +20° C.

It is particularly advantageous to carry out the reaction in a mixture of acetic acid and methylene chloride, in the presence of m-chloroperbenzoic acid, at a temperature of between −10° and 0° C.

If it is desired to obtain the sulphoxide, it is necessary to carry out the reaction with one equivalent of oxidising agent. If it is desired to obtain the sulphone, it is necessary to use at least two equivalents of oxidising agent. The actual oxidation reaction is carried out in the presence of at least one equivalent of an acid such as methanesulphonic acid, at a temperature of the order of 20° C.

According to the invention, the products of the general formula (I) in which A represents a sulphinyl or sulphonyl radical, X represents a sulphur atom, p is equal to 0 and the other symbols are defined as above can be prepared by reacting ammonia or an amine of the general formula (III) with a dithioester of the general formula:

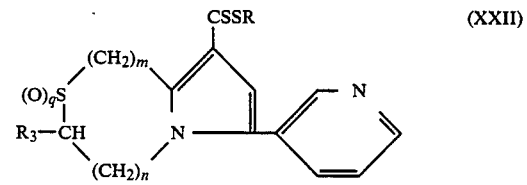
(XXII)

in which R represents an alkyl radical, q is equal to 1 or 2 and the other symbols are defined as above.

The reaction is generally carried in an organic solvent such as ethanol, at a temperature of between 20° C. and the reflux temperature of the reaction mixture.

The dithioesters of the general formula (XXII) can be prepared by oxidising a product of the general formula (XIX) in which A represents a sulphur atom and p is equal to 0, i.e. a product of the general formula:

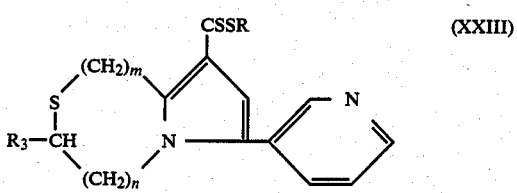
(XXIII)

in which R represents an alkyl radical and $R_3$, m and n are defined as above.

The oxidation is generally carried out under the conditions referred to above for oxidising a product of the general formula (XXI).

According to the invention, the products of the general formula (I) in which m, n, A and $R_3$ are defined as above, X and p are defined as above under (a) and Y represents a radical of the general formula (II) in which $R_1$ represents a hydrogen atom and $R_2$ represents an alkyl radical containing 1 to 5 carbon atoms, which is substituted by a carboxyl radical, can also be prepared by hydrolysing a product of the general formula:

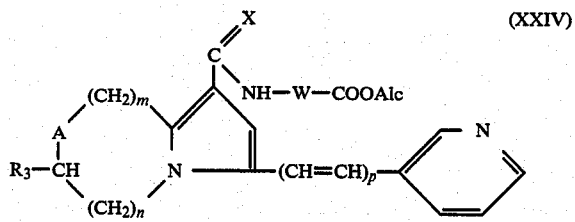
(XXIV)

in which m, n, A, X, $R_3$ and p have the corresponding definitions, Alc represents an alkyl radical and W represents an alkylene radical containing 1 to 5 carbon atoms.

The reaction is carried out by any means known to those skilled in the art for converting an ester to an acid without affecting the rest of the molecule, in particular by saponification by means of an alkali metal hydroxide such as sodium hydroxide or potassium hydroxide, in an alcohol such as ethanol.

The products of the general formula (XXIV) can be prepared by reacting an aminoester of the general formula:

$$H_2N-W-COOAlc \qquad (XXV)$$

in which Alc represents an alkyl radical and W represents an alkylene radical containing to 1 to 5 carbon atoms, with a product of the general formula (IV) if it is desired to obtain the product of the general formula (XXIV) in which X represents an oxygen atom, this being followed, if appropriate, by thionation if it is desired to obtain a product of the general formula (XXIV) in which X represents a sulphur atom, or alternatively with a product of the general formula (XIII) if it is desired to obtain a product of the general formula (XXIV) in which X represents an imino radical.

The reaction can be carried out under the same conditions as those referred to above for reacting a product of the general formula (III) with a product of the general formula (IV) or (XIII).

It is understood by those skilled in the art that, to carry out the processes according to the invention which have been described above, it may be necessary to introduce groups for protecting the functional groups which may be present in the various radicals, in order to prevent secondary reactions. In particular, if a carboxyl or alkoxy carbonyl group is present in the radical $R_2$, it may be necessary to block the said group, e.g. in the form of a 4,4-dimethyl-1,3-oxazoline, and then to regenerate the group by hydrolysis in an aqueous or alcoholic medium after the appropriate process has been carried out. Likewise, if an amino or alkylamino group is present in this radical, it may be necessary to block the said group, e.g. in the form of a trifluoromethylacetamide, and then to regenerate the group by reaction with ammoniacal methanol after the appropriate process has been carried out.

Likewise, if X represents at oxygen atom and Y represents a hydrogen atom, and if it is desired to oxidise a product of the general formula (XXI), it is necessary to block the aldehyde group before carrying out the oxidation, e.g. in the form of an acetal, and then to unblock the aldehyde group by the usual methods.

The new products of the general formula (I) can be purified by the usual known methods, e.g. by crystallisation, chromatography or successive extractions in acidic and basic media.

The compounds of formula (I) can be converted into acid addition salts by reaction with an acid in an organic solvent such as an alcohol, a ketone, an ether or a chlorinated solvent. The salt formed precipitates, if necessary after concentration of its solution. It may be separated off by filtration or decantation.

The compounds of formula (I) in which Y represents a radical of the formula (II) in which $R_1$ represents a hydrogen atom and $R_2$ represents a hydroxyl radical, an alkyl radical containing 1 to 5 carbon atoms, which is substituted by a carboxyl radical, or a phenyl radical substituted by one or more carboxyl radicals can be converted into metal salts or addition salts with nitrogen bases by any method known to those skilled in the art for carrying out this conversion which does not affect the rest of the molecule.

The compounds of formula (I) and their salts possess valuable pharmacological properties, and in particular are useful in the prophylactic and therapeutic treatment of thrombotic complaints. In the test for measuring the in vitro inhibiting activity against platelet aggregation caused by collagen, (using the technique of G. V. R. BORN et al., J. Physiol, 168, 178 (1963)), they have been shown to be active at concentrations of less than 50 mg/liter.

The compounds of formula (I) and their salts also have a low toxicity. Their $LD_{50}$ is generally between 300 and 900 mg/kg, when administered orally to mice.

Of particular value are the compounds of the formula (I) in which m is 1 or 2 and n is zero or 1, A represents sulphur, methylene or sulphonyl, $R_3$ represents hydrogen, alkyl or phenyl, and X represents oxygen, sulphur, imino or hydroxyimino, p is 0 or 1 and Y represents a radical of the formula:

in which $R_1$ and $R_2$ both represent a hydrogen atom, or alternatively $R_1$ represents a hydrogen atom and $R_2$ represents a hydroxyl radical or an alkyl radical containing 1 to 5 carbon atoms, which is substituted by a carboxyl, dialkylamino, hydroxyalkylamino, morpholino or imidazolyl radical or by a piperazin-1-yl radical substituted in the 4 -position by alkyl, or alternatively $R_1$ and $R_2$ form, with the nitrogen atom to which they are bonded, a 6-membered ring which can also contain another hetero atom such as oxygen or nitrogen, and which is unsubstituted or substituted by alkyl, hydroxyalkyl, benzyl or pyrrolidin-1-yl-carbonylalkyl, or X represents dialkylhydrazono, Y represents amino and p is zero, or X and Y form a Δ2-thiazolin-2-yl or Δ2-imidazolin-2-yl radical with the carbon atom to which they are bonded and p is 0, or X represents oxygen, Y represents hydrogen and p is 0.

Of more particular value are the compounds of formula (I) in which m is 1 or 2 and n is zero, A represents sulphur, methylene or sulphonyl, $R_3$ represents a hydrogen atom and X represents oxygen, sulphur, imino or hydroxyimino, p is 0 or 1 and Y represents a radical of the formula:

in which $R_1$ and $R_2$ both represent a hydrogen atom, or $R_1$ represents a hydrogen atom and $R_2$ represents hydroxy or dialkylaminoethyl, or $R_1$ and $R_2$ form, with the nitrogen atom to which they are bonded, a 6-membered ring which can also contain another hetero atom such as nitrogen, and which is unsubstituted or substituted by alkyl or benzyl, or X represents dialkylhydrazono, Y represents amino 20 and p is zero, or X and Y with the carbon atom to which they are bonded from a Δ2-thiazolin-2-yl radical, or X represents oxygen, Y represents hydrogen and p is zero.

Of especial value are the compounds of formula (I) in which m represents 1 or 2 and n represents zero, A represents sulphur, methylene or sulphonyl, $R_3$ represents hydrogen, p is zero, and X represents oxygen, sulphur or hydroxyimino, and Y represents a radical of the formula:

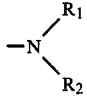

in which $R_1$ and $R_2$ both represent hydrogen, or alternatively $R_1$ and $R_2$ form, with the nitrogen atom to which they are bonded, a piperazin-1-yl ring unsubstituted or substituted by methyl, or X represents dialkylhydrazono and Y represents amino.

The following compounds are of particular value:
5-(pyridin-3-yl)-1H,3H-pyrrolo[1,2-c]thiazole-7-carboxamide;
6-(pyridin-3-yl)-1,2-dihydro-4H-pyrrolo[1,2-c]-1,3-thiazine-8-carboxamide;
5-(pyridin-3-yl)-2,3-dihydro-1H-pyrrolizine-7-carboxamide;
3-(pyridin-3-yl)-5,6,7,8-tetrahydroindolizine-1-carboxamide;
5-(pyridin-3-yl)-1H,3H-pyrrolo[1,2-c]thiazole-7-carbothioamide;
5-(pyridin-3-yl)-1H,3H-pyrrolo[1,2-c]thiazole-7-carboxamide 2,2-dioxide;
7-[(4-methylpiperazin-1-yl)-carbonyl]-5-(pyridin-3-yl)-1H,3H-pyrrolo[1,2-c]thiazole;
5-(pyridin-3-yl)-1H,3H-pyrrolo[1,2-c]thiazole-7-carboxamide-oxime;
5-(pyridin-3-yl)-1H,3H-pyrrolo[1,2-c]thiazole-7-carboxamide-dimethylhydrazone; and
7-(piperazin-1-yl-carbonyl)-5-(pyridin-3-yl)-1H,3H-pyrrolo[1,2-c]thiazole.

For medicinal purposes, the compounds of formula (I) can be used as such or in the form of pharmaceutically acceptable salts, i.e. salts which are non-toxic at the doses used.

Examples of pharmaceutically acceptable salts which may be mentioned are the addition salts with mineral acids, such as the hydrochlorides, sulphates, nitrates and phosphates, or with organic acids, such as the acetates, propionates, succinates, benzoates, fumarates, maleates, methanesulphonates, isethionates, theophyllineacetates, salicylates, phenolphthaleinates and methylene-bis-β-oxynaphthoates, or substitution derivatives of these compounds. Where they exist, salts formed with bases may be used, for example salts with alkali metals, such as the sodium, potassium or lithium salts, and with alkaline earth metals, such as the calcium or magnesium salts, and the addition salts with organic bases, such as the ethanolamine or lysine salts.

The Examples which follow illustrate the invention.

EXAMPLE 1

A suspension of 5-(pyridin-3-yl)-1H,3H-pyrrolo[1,2-c]thiazole-7-carbonitrile (11.35 g) and powdered potassium hydroxide (14 g) in tert.-butyl alcohol (100 cc) is heated at 85° C. for 1 hour. After stirring for 16 hours at a temperature of the order of 20° C., the reaction mixture is poured into distilled water (2 liters). The suspension is stirred at a temperature of the order of 20° C. for 15 minutes and the crystals which have appeared are then filtered off, washed 8 times with distilled water (1,200 cc in total) and then 3 times with ethanol (150 cc in total) and dried under reduced pressure (20 mm Hg; 2.7 kPa) at a temperature of the order of 20° C., in the presence of potassium hydroxide pellets. This gives a crude product (10.5 g), which is combined with a product prepared in the same way in an earlier operation (3.9 g) and dissolved in boiling ethanol (850 cc). The solution is treated with decolourising charcoal (0.5 g) and filtered hot. The filtrate is cooled at a temperature of the order of 4° C. for 3 days. The crystals which have appeared are filtered off, washed 3 times with ethanol cooled to a temperature of the order of 4° C. (30 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carboxamide (11.3 g) in the form of cream crystals melting at 215° C.

The 5-(pyridin-3-yl)-1H,3H-pyrrolo[1,2-c]thiazole-7-carbonitrile can be prepared in the following manner:

A suspension of N-nicotinoylthiazolidine-4-carboxylic acid (403 g) in a mixture of 2-chloroacrylonitrile (1,350 cc) and acetic anhydride (1,750 cc) is heated at 90° C. for 2 hours 40 minutes. During this period, the mixture is seen to pass through a clear homogeneous phase after 30 minutes, this being followed by precipitation 10 minutes later. After cooling at a temperature of the order of 4° C. for 16 hours, the crystals which have appeared are filtered off, washed twice with acetic anhydride (200 cc in total) and 3 times with acetone (300 cc in total) and dried under reduced pressure (20 mm Hg; 2.7 kPa) at a temperature of the order of 20° C., in the presence of potassium hydroxide pellets. The product thus obtained is suspended in a 2N aqueous solution of sodium hydroxide (2,400 cc). After stirring at a temperature of the order of 20° C. for 1 hour 30 minutes, the crystals which have appeared are filtered off, washed 5 times with distilled water (1,250 cc in total), 3 times with ethanol (1,200 cc in total) and 3 times with diethyl ether (900 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carbonitrile (159.7 g) in the form of cream crystals melting at 170° C.

The N-nicotinoylthiazolidine-4-carboxylic acid can be obtained in the following manner:

Nicotinoyl chloride hydrochloride (534 g) is added in the course of 1 hour, at a temperature of between 30° and 52° C., to a solution of thiazolidine-4-carboxylic acid (400 g) and triethylamine (613 g) in chloroform (4,500 cc). The solution obtained is heated at a temperature of the order of 64° C. for 4 hours. After stirring at a temperature of the order of 20° C. for 16 hours, the crystals which have appeared are filtered off, washed 3 times with chloroform (1,500 cc in total) and then 3 times with diethyl ester (1,500 in total) and dried under reduced pressure (20 mm Hg; 2.7 kPa) at a temperature of the order of 20° C., in the presence of potassium hydroxide pellets. This gives N-nicotinoylthiazolidine-4-carboxylic acid (403 g) in the form of white crystals melting at 190° C.

EXAMPLE 2

A suspension of 5-(pyridin-3-yl)-1H,3H-pyrrolo[1,2-c]thiazole-7-carbonitrile (22.7 g) in a mixture of triethylamine (14 cc) and pyridine (32 cc) is saturated for 5 hours, at a temperature of the order of 20° C., with a gaseous stream of hydrogen sulphide. After stirring at a temperature of the order of 20° C. for 3 days, pyridine (32 cc) is added to the reaction mixture, the suspension is saturated again for 8 hours, at a temperature of the order of 20° C., with a gaseous stream of hydrogen sulphide and the stirring is then continued for 16 hours at a temperature of the order of 20° C. The same operation is repeated twice. The suspension is saturated again for a further 3 hours, at a temperature of the order of 20° C., with a gaseous stream of hydrogen sulphide and the reaction mixture is then poured into distilled water (500 cc). The crystals which have appeared are filtered off, washed 4 times with distilled water (200 cc in total), then twice with ethanol (100 cc in total) and then twice with isopropyl ether (100 cc in total) and dried under reduced pressure (20 mm Hg; 2.7 kPa) at a temperature of the order of 20° C., in the presence of potassium hydroxide pellets. This gives a crude product (26 g) melting at 230° C. This product is dissolved in dimethylformamide (250 cc) at a temperature of the order of 100° C. The solution obtained is treated with decolourising charcoal (1 g) and filtered hot; the filtrate is cooled at a temperature of the order 4° C. for 2 hours. The crystals which have appeared are filtered off, washed twice with dimethylformamide (40 cc in total), 3 times with ethanol (150 cc in total) and then 3 times with isopropyl ether (150 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carbothioamide (21 g) in the form of yellow crystals melting at 243° C.

The 5-(pyridin-3-yl)-1H,3H-pyrrolo[1,2-c]thiazole-7-carbonitrile is prepared as described in Example 1.

EXAMPLE 3

A suspension of 5-(pyridin-3-yl)-1H,3H-pyrrolo[1,2-c]thiazole-7-carboxylic acid (8.8 g) in a mixture of thionyl chloride (6.25 cc), dimethylformamide (0.05 cc) and 1,2-dichloroethane (100 cc) is heated under reflux for 2 hours 30 minutes, with stirring. The reaction mixture is cooled to a temperature of the order of 20° C. and concentrated to dryness under reduced pressure (20 mm Hg; 2.7 kPa) at a temperature of the order of 60° C. The residue obtained is suspended in cyclohexane (150 cc) and the solvent is evaporated off under reduced pressure (20 mm Hg; 2.7 kPa) at a temperature of the order of 60° C. The same operation is repeated twice. This gives 7-chloroformyl-5-(pyridin-3-yl)-pyrrolo[1,2-c]lthiazole hydrochloride (10 g) in the form of cream crystals melting at 220° C.

This product is taken up in methylene chloride (200 cc). A solution containing N-(3-aminopropyl)-morpholine (6.2 g) and triethylamine (8.7 g) in methylene chloride (70 cc) is then added to the solution thus obtained in the course of 20 minutes, at a temperature of between 23° and 31° C. The resulting solution is stirred at a temperature of the order of 20° C. for 16 hours. Methylene chloride (250 cc) and distilled water (250 cc) are added to the solution. The organic phase is separated off, washed twice with distilled water (500 cc in total), treated with decolourising charcoal (0.5 g), dried over anhydrous magnesium sulphate and filtered, and the filtrate is concentrated to dryness under reduced pressure (20 mm Hg; 2.7 kPa) at a temperature of the order of 60° C. This gives a crude oil (1.6 g). This product is combined with a product prepared in the same way in a previous operation (2.7 g) and is dissolved in boiling propan-2-ol (150 cc). Decolourising charcoal (0.5 g) is added to the solution obtained and the mixture is filtered hot. The filtrate is cooled at a temperature of the order of 4° C. for 1 hour. The crystals which have appeared are filtered off, washed 3 times with propan-2-ol (30 cc in total) and 3 times with isopropyl ether (75 cc in total) and dried under reduced pressure (20 mm Hg; 2.7 kPa) at a temperature of the order of 20° C., in the presence of potassium hydroxide pellets. This gives a product (11.6 g) melting at 156° C. This product is dissolved in boiling ethanol (50 cc). Decolourising charcoal (0.5 g) is added to the solution obtained and the mixture is filtered hot. The filtrate is cooled at a temperature of the order of 4° C. for 1 hour. The crystals which have appeared are filtered off, washed twice with ethanol (10 cc in total) and then 3 times with isopropyl ether (75 cc in total) and dried under reduced pressure (20 mm Hg; 2.7 kPa) at a temperature of the order of 20° C., in the presence of potassium hydroxide pellets. This gives a product (10.5 g) melting at 158° C. This product is dissolved in boiling acetonitrile (200 cc). The solution obtained is filtered hot and the filtrate is then cooled at a temperature of the order of 4° C. for 15 minutes. The crystals which have appeared are filtered off, washed 3 times with acetonitrile (45 cc in total) and 3 times with isopropyl ether (75 cc in total) and dried under reduced pressure (20 mm Hg; 2.7 kPa) at at temperature of the order of 20° C., in the presence of potassium hydroxide pellets. This gives N-(3-morpholino-propyl)-5-(pyridin-3-yl)-1H,3H-pyrrolo[1,2-c]thiazole-7-carboxamide (9 g) in the form of cream crystals melting at 158° C.

The 5-(pyridin-3-yl)-1H,3H-pyrrolo[1,2-c]thiazole-7-carboxylic acid can be prepared in the following manner:

A mixture of 5-(pyridin-3-yl)-1H,3H-pyrrolo[1,2-c]thiazole-7-carbonitrile (18.7 g), potassium hydroxide pellets (16.3 g) and ethylene glycol (160 cc) is heated at a temperature of the order of 155° C. for 2 hours, with stirring. After stirring for 16 hours at a temperature of the order of 20° C., the solvent is evaporated off under reduced pressure (2 mm Hg; 0.27 kPa) at a temperature of the order of 100° C. The residue is dissolved in distilled water (100 cc) and the solution obtained is brought to a pH of the order of 5 by adding a 2N aqueous solution of hydrochloric acid. The crystals which have appeared are filtered off, washed 3 times with distilled water (150 cc in total) and then 3 times with acetone (150 cc in total) and dried under reduced pressure (20 mm Hg; 2.7 kPa) at a temperature of the order of 20° C., in the presence of potassium hydroxide pellets. This gives a crude product (17.7 g) melting at 264° C. This product is combined with a product prepared in the same way in a previous operation (1.3 g) and dissolved in a mixture of butan-1-ol (650 cc) and dimethylformamide (150 cc), heated beforehand to a temperature of the order of 115° C. Decolourising charcoal (0.5 g) is added to the solution obtained and the mixture is filtered hot. The filtrate is cooled at a temperature of the order of 4° C. for 16 hours. The crystals which have appeared are filtered off, washed twice with dimethylformamide (50 cc in total), 3 times with ethanol (150 cc in total), 3 times with isopropyl ether (150 cc in total) and then 3 times with diethyl ether (150 cc in total) and dried under reduced pressure (20 mm Hg; 2.7 kPa) at a temperature of the order of 20° C., in the presence of potassium hydroxide pellets. This gives a product (16.1 g) melting at 266° C. This product is suspended in distilled water (250 cc) and the suspension is stirred at a temperature of the order of 20° C. for 2 hours. The crystals are filtered off, washed 5 times with distilled water (150 cc in total), 3 times with ethanol (90 cc in total), 3 times with isopropyl ether (90 cc in total) and then 3 times with diethyl ether (90 cc in total) and dried under reduced pressure (20 mm Hg; 2.7 kPa) at a temperature of the order of 100° C., in the presence of potassium hydroxide pellets. This gives 5-(pyridin-3-yl)-1H,3H-pyrrolo[1,2-c]thiazole-7-carboxylic acid (15.5 g) in the form of cream crystals melting at 266° C.

The 5-(pyridin-3-yl)-1H,3H-pyrrolo[1,2-c]thiazole-7-carbonitrile is prepared as in Example 1.

EXAMPLE 4

A solution of N-methylpiperazine (13.2 g) in methylene chloride (120 cc) is added in the course of 20 minutes, at a temperature of between 22° and 30° C., to a suspension of 7-chloroformyl-5-(pyridin-3-yl)-1H,3H-pyrrolo[1,2-c]thiazole hydrochloride (12.5 g) in methylene chloride (250 cc). The solution obtained is stirred at a temperature of the order of 20° C. for 16 hours. Methylene chloride (250 cc) and distilled water (150 cc) are then added. The organic phase is separated off by decantation, washed twice with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. The hard foam obtained is taken up in isopropyl ether (150 cc) for 1 hour at a temperature of the order of 20° C., with stirring. After 24 hours at this temperature, the crystals which have appeared are filtered off, washed 3 times with isopropyl ether (75 cc in total) and dried under reduced pressure (20 mm Hg; 2.7. kPa) at a temperature of the order of 20° C., in the presence of potassium hydroxide pellets. This gives a crude product (10.8 g) melting at 90° C. This product is dissolved in boiling carbon tetrachloride (250 cc). Decolourising charcoal (0.5 g) is added to the solution obtained and the mixture is filtered hot; the filtrate is cooled at a temperature of the order of 4° C. for 16 hours. The crystals which have appeared are filtered off, washed 3 times with carbon tetrachloride (30 cc in total) and then 4 times with isopropyl ether (100 cc in total) and dried under reduced pressure (20 mm Hg; 2.7 kPa) at a temperature of the order of 20° C., in the presence of potassium hydroxide pellets. This gives a product (5.8 g) melting at 104° C. This product (5.4 g) is dissolved in boiling acetonitrile (12 cc). The solution obtained is cooled at a temperature of the order of 4° C. for 2 hours. The crystals which have appeared are filtered off, washed 3 times with acetonitrile (6 cc in total) and 3 times with isopropyl ether (30 cc in total) and dried under reduced pressure (20 mm Hg; 2.7 kPa) at a temperature of the order of 20° C., in the presence of potassium hydroxide pellets. This gives 7-[(4-methylpiperazin-1-yl)-carbonyl]-5-(pyridin-3-yl)-1H,3H-pyrrolo[1,2-c]thiazole (4 g) in the form of cream crystals melting at 108° C.

The 7-chloroformyl-5-(pyridin-3-yl)-1H,3H-pyrrolo[1,2-c]thiazole hydrochloride is prepared as in Example 3.

EXAMPLE 5

A suspension of 5-(pyridin-3-yl)-2,3-dihydro-1H-pyrrolizine-7-carbonitrile (14.6 g) and powdered potassium hydroxide (23.1 g) in tert.-butyl alcohol (140 cc) is heated at 82° C. for 2 hours. During this period, the mixture is seen to pass through a clear homogeneous phase after 10 minutes, this being followed by precipitation 20 minutes later. After cooling to a temperature of the order of 20° C., the solvent is evaporated off under reduced pressure (20 mm Hg; 2.7 kPa) at a temperature of the order of 60° C. The crystalline residue obtained is suspended in distilled water (250 cc) and the suspension is stirred at a temperature of the order of 20° C. for 30 minutes. The crystals are filtered off, washed 4 times with distilled water (200 cc in total) and then 3 times with isopropyl ether (150 cc in total) and dried reduced pressure (20 mm Hg; 2.7 kPa) at a temperature of the order of 20° C., in the presence of potassium hydroxide pellets. This gives a crude product (15.5 g) melting at 206° C. This product is dissolved in boiling ethanol (150 cc). The solution obtained is treated with decolourising charcoal (0.5 g) and filtered; the filtrate is cooled at a temperature of the order of 10° C. for 2 hours. The crystals are filtered off and dried under reduced pressure (20 mm Hg; 2.7 kPa) at a temperature of the order of 20° C., in the presence of potassium hydroxide pellets. This gives 5-(pyridin-3-yl)-2,3-dihydro-1H-pyrrolizine-7-carboxamide (9.6 g) in the form of cream crystals melting at 210° C.

The 5-(pyridin-3-yl)-2,3-dihydro-1H-pyrrolizine-7-carbonitrile can be prepared in the following manner:

A suspension of N-nicotinoyl-L-proline (44 g) in a mixture of 2-chloroacrylonitrile (160 cc) and acetic anhydride (200 cc) is heated gradually to 90° C. After the reactants have dissolved in the reaction medium, precipitation is observed, giving rise to a suspension. The heating of the suspension is continued for 3 hours 30 minutes at a temperature of the order of 90° C. After cooling at a temperature of the order of 4° C. for 1 hour, the crystals which have appeared are filtered off, washed twice with acetic anhydride (50 cc in total) and 3 times in acetone (300 cc in total) and dried under reduced pressure (20 mm Hg; 2.7 kPa) at a temperature of the order of 20° C., in the presence of potassium hydroxide pellets. The product thus obtained is taken up in a 1N aqueous solution of sodium hydroxide (500 cc). The oil which has appeared is dissolved in ethyl acetate (250 cc). The organic phase is separated off by decantation and the aqueous phase is extracted 3 times with ethyl acetate (750 cc in total). The organic extracts are combined, washed 3 times with distilled water (750 cc in total), dried over anhydrous potassium carbonate, treated with decolourising charcoal (1 g) and filtered, and the filtrate is concentrated to dryness under reduced pressure (20 mm Hg; 2.7 kPa) at a temperature of the order of 60° C. This gives a crude product (25.2 g). This product is chromatographed on a column of diameter 4 cm, containing silica (0.063—0.2 mm) (250 g), elution being carried out with ethyl acetate and 400 cc fractions being collected. The first two fractions are discarded and the next three fractions are combined and concentrated to dryness under reduced pressure (20 mm Hg; 2.7 kPa) at a temperature of the order of 60° C. This gives a product (21 g). This product is dissolved in boiling ethanol (100 cc). The solution obtained is cooled at a temperature of the order of 4° C. for 1 hour. The crystals which have appeared are filtered off and washed 3 times with ethanol cooled to a temperature of the order of 4° C. (30 cc in total) and then 3 times with isopropyl ether (150 cc in total). This gives 5-(pyridin-3-yl)-2,3-dihydro-1H-pyrrolizine-7-carbonitrile (16.1 g) in the form of cream crystals melting at 112° C.

The N-nicotinoyl-L-proline can be prepared according to F. COUSTOU and B. BELLEGARDE, West German Pat. No. 2,537,590.

EXAMPLE 6

A solution of 2-diethylaminoethylamine (13.9 g) in methylene chloride (50 cc) is added in the course of 20 minutes, at a temperature of the order of 20° C., to a suspension of 7-chloroformyl-5-(pyridin-3-yl)-1H,3H-pyrrolo[1,2-c]thiazole hydrochloride (12 g) in methylene chloride (200 cc). The solution obtained is stirred for 16 hours at a temperature of the order of 20° C. A product precipitates. Methylene chloride (250 cc) and a 2N aqueous solution of sodium hydroxide (100 cc) are then added; the organic phase is separated off by decantation, washed with a 2N aqueous solution of sodium hydroxide (100 cc) and then 3 times with distilled water (600 cc in total), dried over anhydrous potassium carbonate, treated with decolourising charcoal (0.5 g) and filtered, and the filtrate is concentrated to dryness under reduced pressure (20 mm Hg; 2.7 kPa) at a temperature of the order of 60° C. This gives a crude product (12 g). This product is dissolved in boiling acetonitrile (60 cc). The solution obtained is treated with decolourising charcoal (0.5 g) and filtered hot; the filtrate is cooled at a temperature of the order of 4° C. for 2 hours. The crystals which have appeared are filtered off, washed twice with acetonitrile cooled to a temperature of the order of 4° C. (20 cc in total) and then 3 times with isopropyl ether (150 cc in total) and dried under reduced pressure (20 mm Hg; 2.7 kPa) at a temperature of the order of 20° C., in the presence of potassium hydroxide pellets. This gives N-(2-diethylaminoethyl)-5-(pyridin-3-yl)-1H,3H-pyrrolo[1,2-c]thiazole-7-carboxamide (6.4 g) in the form of light beige crystals melting at 106° C.

The 7-chloroformyl-5-(pyridin-3-yl)-1H,3H-pyrrolo[1,2-c]thiazole hydrochloride is prepared as in Example 3.

EXAMPLE 7

Mercuric chloride (10.9 g) is added in the course of 10 minutes, at a temperature of between 20° and 30° C., to a suspension of 5-(pyridin-3-yl)-1H,3H-pyrrolo[1,2-c]thiazole-7-carbothioamide (10.4 g) and hydroxylamine hydrochloride (8.4 g) in pyridine (100 cc). The suspension obtained is stirred at a temperature of the order of 20° C. for 48 hours and is then poured into distilled water (1,000 cc). The precipitate is filtered off, washed 3 times with distilled water (300 cc in total) and extracted continuously for 4 hours with boiling methanol (750 cc) using a Soxhlet extractor. This gives a product (8 g). This product is dissolved in a 0.5N aqueous solution of hydrochloric acid (130 cc). The solution obtained is treated with decolourising charcoal (0.5 g) and filtered, and the filtrate is diluted with distilled water (150 cc) and brought to a pH of the order of 10 by adding a 5N aqueous solution of sodium hydroxide. The crystals which have appeared are filtered off, washed 3 times with distilled water (150 cc in total), twice with ethanol (50 cc in total) and then with diethyl ether (50 cc) and dried under reduced pressure (20 mm Hg; 2.7 kPa) at a temperature of the order of 20° C., in the presence of potassium hydroxide pellets. This gives a crude product (5.8 g) melting at 200° C. This product is chromatographed on a column of diameter 2.5 cm, containing silica (0.063–0.2 mm) (60 g), 100 cc fractions being collected. The first 3 fractions from elution with pure methylene chloride, the next 2 fractions from elution with a mixture of methylene chloride and methanol (98/2 by volume), the next 2 fractions from elution with a mixture of methylene chloride and methanol (96/4 by volume) and the next 2 fractions from elution with a mixture of methylene chloride and methanol (94/6 by volume) are discarded. The next 7 fractions from elution with a mixture of methylene chloride and methanol (90/10 by volume) and the next 4 fractions from elution with a mixture of methylene chloride and methanol (80/20 by volume) are combined and concentrated to dryness under reduced pressure (20 mm Hg; 2.7 kPa) at a temperature of the order of 40° C. This gives a product (5 g) melting at 208° C. This product is dissolved in a mixture of butan-1-ol (35 cc) and dimethylformamide (25 cc) at a temperature of the order of 115° C. The solution obtained is treated with decolourising charcoal (0.5 g) and filtered; the filtrate is cooled at a temperature of the order of 4° C. for 2 hours. The crystals which have appeared are filtered off, washed twice with butan-1-ol (20 cc in total), twice with ethanol (50 cc in total) and then 3 times with isopropyl ether (150 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carboxamide-oxime (3.7 g) in the form of cream crystals melting at 214° C.

The 5-(pyridin-3-yl)-1H,3H-pyrrolo[1,2-c]thiazole-7-carbothioamide is prepared as in Example 2.

EXAMPLE 8

A suspension of S-methyl 5-(pyridin-3-yl)-1H,3H-pyrrolo[1,2-c]thiazole-7-thiocarboximidate hydroiodide (20.2 g) and N,N-dimethylhydrazine (3.4 g) in ethanol (100 cc) is heated at the boil for 5 hours 30 minutes and then filtered hot. After cooling to a temperature of the order of 20° C., diethyl ether (350 cc) is added to the filtrate. The suspension obtained is stirred at a temperature of the order of 20° C. for 30 minutes. The crystals which have appeared are filtered off, washed twice with a mixture of ethanol and diethyl ether (50/50 by volume) (100 cc in total) and dried under reduced pressure (20 mm Hg; 2.7 kPa) at a temperature of the order of 20° C., in the presence of potassium hydroxide pellets. The product obtained is suspended in a mixture of water (300 cc) and ethyl acetate (300 cc). A 10N aqueous solution of sodium hydroxide (100 cc) is added to this suspension. The organic phase is separated off by decantation and the aqueous phase is extracted twice with ethyl acetate (300 cc in total). The organic extracts are combined, washed 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (9.3 g) melting at 168° C. This product is dissolved in boiling ethanol (100 cc). The solution obtained is treated with decolourising charcoal (0.5 g) and filtered hot; the filtrate is cooled at a temperature of the order of 4° C. for 1 hour. The crystals which have appeared are filtered off, washed 3 times with ethanol cooled to a temperature of the order of 4° C. (30 cc in total) and 3 times with isopropyl ether (60 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carboxamide-dimethylhydrazone (4.95 g) in the form of cream crystals melting at 170° C.

The S-methyl 5-(pyridin-3-yl)-1H,3H-pyrrolo[1,2-c]thiazole-7-thiocarboximidate hydroiodide can be prepared in the following manner:

A suspension of 5-(pyridin-3-yl)-1H,3H-pyrrolo[1,2-c]thiazole-7-carbothioamide (81.3 g) and methyl iodide (49 g) in a mixture of acetone (3,110 cc) and dimethylformamide (1,550 cc) is stirred at a temperature of the order of 20° C. for 3 days. The crystals which have appeared are filtered off, washed 3 times with acetone (1,500 cc in total) and then twice with diethyl ether (500 cc in total) and dried under reduced pressure (20 mm Hg; 2.7 kPa) at a temperature of the order of 20° C., in the presence of potassium hydroxide pellets. This gives S-methyl 5-(pyridin-3-yl)-1H,3H-pyrrolo[1,2-c]thiazole-7-thiocarboximidate hydroiodide (113 g) in the form of yellow crystals melting at 262° C.

The 5-(pyridin-3-yl)-1H,3H-pyrrolo[1,2-c]thiazole-7-carbothioamide can be prepared as in Example 2.

EXAMPLE 9

Triethylamine (26.5 g) is added in the course of 20 minutes, at a temperature of between 16° and 27° C., to a suspension of 7-chloroformyl-5-(pyridin-3-yl)-1H,3H-pyrrolo[1,2-c]thiazole hydrochloride (15.7 g) and hydroxylamine hydrochloride (10.9 ) in methylene chloride (390 cc). The solution obtained is stirred for 16 hours at a temperature of the order of 20° C. The crystals which have appeared are filtered off, washed 3 times with methylene chloride (150 cc in total) and dried under reduced pressure (20 mm Hg; 2.7 kPa) at a temperature of the order of 20° C., in the presence of potassium hydroxide pellets. The crystals obtained are suspended in distilled water (250 cc) at a temperature of the order of 20° C. for 70 minutes, with stirring. The crystals are filtered off, washed 3 times with distilled water (150 cc in total), 3 times with acetone (150 cc in total) and 3 times with diethyl ether (150 cc in total) and dried under reduced pressure (20 mm Hg; 2.7 kPa) at a temperature of the order of 20° C., in the presence of potassium hydroxide pellets. This gives a crude product (11.6 g) melting at 195° C. This product, combined with a product originating from an earlier operation (2 g), is dissolved in boiling butan-1-ol (500 cc). Decolourising charcoal (0.5 g) is added to the solution obtained and the mixture is filtered; the filtrate is cooled at a temperature of the order of 4° C. for 1 hour. The crystals which have appeared are filtered off, washed twice with butan-1-ol (50 cc in total), 3 times with ethanol (150 cc in total) and then 3 times with diethyl ether (150 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carbohydroxamic acid (8.4 g) in the form of ochre-coloured crystals melting at 210° C.

The 7-chloroformyl-5-(pyridin-3-yl)-1H,3H-pyrrolo[1,2-c]thiazole hydrochloride is prepared as in Example 3.

EXAMPLE 10

A suspension of S-methyl 5-(pyridin-3-yl)-1H,3H-pyrrolo[1,2-c]thiazole-7-thiocarboximidate hydroiodide (20.2 g), piperidine (8.6 g) and acetic acid (10.5 g) in chloroform (500 cc) is stirred at 20° C. for 3 days. A 2.8N aqueous solution of sodium hydroxide (360 cc) and chloroform (200 cc) are then added to the suspension. The organic phase is separated off by decantation and the aqueous phase is extracted twice with chloroform (1,000 cc in total). The organic extracts are combined, washed 3 times with distilled water (750 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a product (15 g), which is taken up in boiling ethyl acetate (200 cc). After cooling to a temperature of the order of 20° C., the crystals which have appeared are filtered off and the filtrate is concentrated to dryness under reduced pressure (20 mm Hg; 2.7 kPa)

at a temperature of the order of 60° C. This gives a product (14.1 g). This product is dissolved in ethanol (130 cc) and the solution obtained is treated with a 4.7N ethanolic solution of hydrogen chloride (19.3 cc) and is then cooled at a temperature of the order of 4° C. for 1 hour. The crystals which have appeared are filtered off, washed 3 times with ethanol (75 cc in total) and 3 times with diethyl ether (150 cc in total) and dried under reduced pressure (20 mm Hg; 2.7 kPa) at a temperature of the order of 20° C., in the presence of potassium hydroxide pellets. This gives a crude product (13.7 g) in the form of the dihydrochloride, melting at 264° C. This product is combined with a product prepared in a previous operation (2.4 g) and is dissolved in distilled water (200 cc). A 1N aqueous solution of sodium hydroxide (84 cc) and ethyl acetate (250 cc) are added to the solution obtained. The organic phase is separated off by decantation and the aqueous phase is extracted twice with ethyl acetate (200 cc in total). The organic extracts are combined, dried over anhydrous potassium carbonate, treated with decolourising charcoal (0.5 g) and filtered, and the filtrate is concentrated to dryness under reduced pressure (20 mm Hg; 2.7 kPa) at a temperature of the order of 60° C. This gives a product (13 g). This product is chromatographed on a column of diameter 2.4 cm, containing silica (0.063–0.2 mm) (65 g), elution being carried out with mixtures of acetonitrile and aqueous ammonia (d=0.92) and 100 cc fractions being collected. The first 2 fractions from elution from a mixture of acetonitrile and aqueous ammonia (95/5 by volume) are discarded. The third fraction from elution with a mixture of acetonitrile and aqueous ammonia (95/5 by volume) and the next 9 fractions from elution with a mixture of acetonitrile and aqueous ammonia (90/10 by volume) are combined and concentrated to dryness under reduced pressure (20 mm Hg; 2.7 kPa) at a temperature of the order of 40° C. This gives a product (11.3 g). This product is chromatographed again on a column of diameter 6 cm, containing silica (0.04–0.063 mm) (480 g). Elution is carried out with a mixture of methylene chloride, methanol and 20% strength aqueous ammonia (12/6/1 by volume) under a pressure of 0.5 bar (51 kPa), 100 cc fractions being collected. The first 7 fractions are discarded and the next 14 fractions are combined and concentrated to dryness under reduced pressure (20 mm Hg; 2.7 kPa) at a temperature of the order of 40° C. This gives a product (9.6 g). This product is taken up in boiling ethyl acetate (350 cc) and the suspension obtained is filtered hot; the filtrate is then cooled to a temperature of the order of 20° C. and concentrated to dryness under reduced pressure (20 mm Hg; 2.7 kPa) at a temperature of the order of 60° C. This gives a product (9.1 g). This product is dissolved in ethanol (100 cc). The solution obtained is treated with 4.7N ethanolic solution of hydrogen chloride (12.4 cc) and is cooled at a temperature of the order of 4° C. for 2 hours. The crystals which have appeared are filtered off, washed twice with ethanol cooled at a temperature of the order of 4° C. (50 cc in total) and then 3 times with diethyl ether (150 cc in total) and dried under reduced pressure (20 mm Hg; 2.7 kPa) at a temperature of the order of 20° C., in the presence of potassium hydroxide pellets. This gives a product (9.7 g). This product is dissolved in a boiling mixture of ethanol (175 cc) and distilled water (10 cc). The solution obtained is treated with decolourising charcoal (0.5 g) and filtered hot; the filtrate is cooled at a temperature of the order of 4° C. for 3 hours. The crystals which have appeared are filtered off, washed 3 times with ethanol (30 cc in total) and 3 times with diethyl ether (75 cc in total) and dried under reduced pressure (20 mm Hg; 2.7 kPa) at a temperature of the order of 20° C., in the presence of potassium hydroxide pellets. This gives 7-piperidinocarbonimidoyl-5-(pyridin-3-yl)-1H,3H-pyrrolo[1,2-c]thiazole dihydrochloride (4.5 g) in the form of pale yellow crystals melting at 284° C.

The S-methyl 5-(pyridin-3-yl)-1H,3H, pyrrolo[1,2-c]thiazole-7-thiocarboximidate hydroiodide is prepared as in Example 8.

EXAMPLE 11

A suspension of S-methyl 5-(pyridin-3-yl)-1H,3H-pyrrolo[1,2-c]thiazole-7-thiocarboximidate hydroiodide (52.4 g), ammonia acetate (20 g) and acetic acid (27.3 g) in chloroform (1,300 cc) is heated at the boil for 20 hours, with stirring. The suspension is then cooled to a temperature of the order of 20° C. and the crystals are filtered off, washed 3 times with chloroform (450 cc in total) and 3 times with diethyl ether (450 cc in total) and dried under reduced pressure (20 mm Hg; 2.7 kPa) at a temperature of the order of 20° C., in the presence of potassium hydroxide pellets. This gives a product (52 g). This product (49.5 g) is dissolved in boiling distilled water (1,800 cc). The solution obtained is cooled to a temperature of the order of 50° C. and treated with ethyl acetate (600 cc) and a 10N aqueous solution of sodium hydroxide (250 cc). After stirring for 10 minutes at a temperature of the order of 50° C. and then cooling to a temperature of the order of 20° C., followed by decantation, the organic phase is discarded and the aqueous phase is extracted twice with ethyl acetate (1,100 cc). The aqueous phase is treated with a mixture of ethyl acetate (1,100 cc) and a 10N aqueous solution of sodium hydroxide (2,800 cc) the temperature being kept at about 25° C. The organic phase is separated off by decantation and the aqueous phase is extracted twice with ethyl acetate (1,200 cc in total). The organic extracts are combined, washed 3 times with distilled water (750 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a product (14.5 g). This product is dissolved in boiling methanol (200 cc). The solution obtained is treated with decolourising charcoal (0.5 g) and filtered; the filtrate is cooled at a temterperature of the order of 4° C. for 3 days. The crystals which have appeared are filtered off, washed twice with methanol cooled to a temperature of the order of 4° C. (20 cc) and then 3 times with diethyl ether (75 cc in total) and dried under reduced pressure (20 mm Hg; 2.7 kPa) at a temperature of the order of 20° C., in the presence of potassium hydroxide pellets. This gives a product (8.3 g). This product is dissolved in distilled water (150 cc). The solution obtained is treated with a 10N aqueous solution of sodium hydroxide (150 cc). The suspension obtained is stirred at a temperature of the order of 20° C. for 3 hours. The crystals which have appeared are filtered off, washed 5 times with distilled water (170 cc in total) and dried under reduced pressure (20 mm Hg; 2.7 kPa) at a temperature of the order of 20° C., in the presence of potassium hydroxide pellets. This gives a crude product (5.5 g). This product is combined with a product prepared in the same manner in a previous operation (4.3 g) and dissolved in boiling ethanol (180 cc). The solution obtained is treated with decolourising charcoal (0.5 g) and filtered; the filtrate is cooled at a temperature of the order of 4° C. for 2 hours. The crystals which have appeared are filtered off, washed 3 times with ethanol cooled to a temperature of the order of 4° C. (30 cc in total) and 3 times with diethyl ether (75 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carboxamidine (6.5 g) in the form of cream crystals melting at 200° C.

The S-methyl 5-(pyridin-3-yl)-1H,3H-pyrrolo[1,2-c]thiazole-7-thiocarboximidate hydroiodide is prepared as in Example 8.

EXAMPLE 12

A suspension of 6-(pyridin-3-yl)-3,4-dihydro-1H-pyrrolo[2,1-c]-1,4-thiazine-8-carbonitrile (4.9 g) and powdered potassium hydroxide (6.7 g) in tert.-butyl alcohol (50 cc) is heated at the boil for 1 hour 15 minutes. The solvent is then evaporated off under reduced pressure (20 mm Hg; 2.7 kPa) at a temperature of the order of 60° C. and the residue is then suspended in distilled water (150 cc). The crystals which have appeared are filtered off, washed 3 times with distilled water (150 cc in total) and dried under reduced pressure (20 mm Hg; 2.7 kPa) at a temperature of the order of 20° C. This gives a crude product (5.2 g) melting at 186° C. This product is combined with a product prepared in the same way in previous operations (4.5 g) and is dissolved in boiling ethanol (250 cc). The solution obtained is treated with decolourising charcoal (0.5 g) and then filtered hot; the filtrate is cooled at a temperature of the 4° C. for 2 hours. The crystals which have appeared are filtered off, washed twice with ethanol cooled to a temperature of the order of 4° C. (50 cc in total) and then 3 times with diethyl ether (75 cc in total) and dried under reduced pressure (20 mm Hg; 2.7 kPa) at a temperature of the order of 20° C., in the presence of potassium hydroxide pellets. This gives 6-(pyridin-3-yl)-3,4-dihydro-1H-pyrrolo[2,1-c]-1,4-thiazine-8-carboxamide (7.1 g) in the form of yellow crystals melting at 192° C.

The 6-(pyridin-3-yl)-3,4-dihydro-1H-pyrrolo[2,1-c]-1,4-thiazine-8-carbonitrile can be prepared in the following manner:

A suspension of N-nicotinoyl-1,4-thiazine-3-carboxylic acid (27.9 g) in a mixture of 2-chloroacrylonitrile (89 cc) and acetic anhydride (117 cc) is heated gradually. When the temperature reaches 70° C., the temperature is seen to rise to 90° C. and the suspended material dissolves, this being followed, after 5 minutes at this temperature, by crystallisation, producing a suspension. Heating is continued at a temperature of the order of 90° C. for 2 hours and the reaction mixture is then cooled to a temperature of the order of 20° C. The crystals are filtered off, washed 3 times with acetic anhydride (75 cc in total) and then 3 times with acetone (150 cc in total) and dried under reduced pressure (20 mm Hg; 2.7 kPa) at a temperature of the order of 20° C., in the presence of potassium hydroxide pellets. This gives a product (6.3 g). This product is suspended in distilled water (100 cc). The suspension obtained is treated with a 5N aqueous solution of sodium hydroxide (50 cc) and then extracted 3 times with ethyl acetate (300 cc in total). The organic extracts are combined, washed 3 times with distilled water (150 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This 6-(pyridin-3-yl)-3,4-dihydro-1H-pyrrolo[2,1-c]-1,4-thiazine-8-carbonitrile (5 g) in the form of light orange crystals melting at 150° C.

The N-nicotinoyl-1,4-thiazine-3-carboxylic acid can be prepared in the following manner:

A solution of ethyl N-nicotinoyl-1,4-thiazine-3-carboxylate (2.8 g) in a mixture of ethanol (25 cc) and a 2N aqueous solution of sodium hydroxide (10 cc) is stirred at a temperature of the order of 20° C. for 3 hours. The solvent is then evaporated off under reduced pressure (20 mm Hg; 2.7 kPa) at a temperature of the order of 50° C. The product obtained is dissolved in distilled water (50 cc) and purified by passing this solution over DOWEX 50WX-2 resin (50-100 mesh) (30 g) contained in a column of diameter of 1.6 cm. The first fraction from elution with distilled water, the second fraction from elution with methanol and the third fraction from elution with distilled water are discarded, as are also the next 2 fractions from elution with a 2% strength (v/v) aqueous solution of pyridine. The next 2 fractions from elution with a 2% strength (v/v) aqueous solution of pyridine are combined and concentrated to dryness under reduced pressure (20 mm Hg; 2.7 kPa) at a temperature of the order of 50° C. This gives a crude product (2.3 g). This product is dissolved in boiling methanol (50 cc) and the solution obtained is cooled at a temperature of the order of 4° C. for 1 hour. The crystals which have appeared are filtered off, washed twice with methanol (100 cc in total) and then 3 times with isopropyl ether (45 cc in total) and dried under reduced pressure (20 mm Hg; 2.7 kPa) at a temperature of the order of 20° C., in the presence of potassium hydroxide pellets. This gives N-nicotinoyl-1,4-thiazine-3-carboxylic acid (1.5 g) in the form of white crystals melting at 212° C.

The ethyl N-nicotinoyl-1,4-thiazine-3-carboxylate can be obtained in the following manner.

Nicotinoyl chloride hydrochloride (8.9 g) is added in the course of 25 minutes, at a temperature of between 24° C. and 38° C., to a solution of ethyl 1,4-thiazine-3-carboxylate (8.8 g) and triethylamine (10.1 g) in chloroform (125 cc). The solution obtained is stirred for 3 hours at a temperature of the order of 20° C. and triethylamine (10.1 g) is then added, followed in the course of 15 minutes, at a temperature of between 24° C. and 36° C., by nicotinoyl chloride hydrochloride (8.9 g). The solution obtained is stirred for 16 hours at a temperature of the order of 20° C. and then for 2 hours at the boil. The reaction mixture is cooled to a temperature of the order of 20° C. and treated with a mixture of chloroform (250 cc) and distilled water (100 cc). The organic phase is separated off by decantation, washed with distilled water (100 cc) and then twice with a 2N aqueous solution of sodium hydroxide (300 cc in total) and twice with distilled water (200 cc in total), dried over anhydrous potassium carbonate, treated with decolourising charcoal (0.5 g) and filtered, and the filtrate is concentrated to dryness under reduced pressure (20 mm Hg; 2.7 kPa) at a temperature of the order of 60° C. This gives a crude product (17.5 g). This product is chromatographed on a column of diameter 6 cm, containing silica (0.04–0.063 mm) (480 g). Elution is carried out with a mixture of ethyl acetate and methanol (98/2 by volume) under a pressure of 0.5 bar (51 kPa), 100 cc fractions being collected. The first 14 fractions are discarded; the next 9 fractions are combined and concentrated to dryness under reduced pressure (20 mm Hg;

2.7 kPa) at a temperature of the order of 60° C. This gives ethyl N-nicotinoyl-1,4-thiazine-3-carboxylate (9.6 g) in the form of a yellow oil.

[Rf=0.35; chromatography on a thin layer of silica gel; solvent: ethyl acetate/methanol (98/2 by volume)].

The ethyl 1,4-thiazine-3-carboxylate can be obtained according to B. BELLEAU, J. Med. Pharm. Chem. 2, 553 (1960).

EXAMPLE 13

A suspension of N-nicotinoyl-3,4,5,6-tetrahydro-2H-1,3-thiazine-4-carboxylic acid (21.5 g) and 2-chloroacrylamide (32 g) in acetic anhydride (250 cc) is heated at a temperature of the order of 75° C. for 15 minutes and then at a temperature of the order of 95° C. for 1 hour. The suspension obtained is then cooled at a temperature of the order of 4° C. for 1 hour and the crystals are filtered off, washed 3 times with acetic anhydride (15 cc in total) and then 3 times with diethyl ether (45 cc in total) and dried under reduced pressure (20 mm Hg; 2.7 kPa) at a temperature of the order of 20° C., in the presence of potassium hydroxide pellets. This gives a product (16.1 g). This product is dissolved in distilled water (750 cc) at a temperature of the order of 45° C. and the solution obtained is then brought to a pH of the order of 8 by adding sodium bicarbonate. The suspension obtained is cooled at a temperature of the order of 4° C. for 70 minutes and the crystals are filtered off, washed 3 times with distilled water (240 cc in total), 3 times with ethanol (10 cc in total) and 3 times with diethyl ether (30 cc in total) and dried under reduced pressure (20 mm Hg; 2.7 kPa) at a temperature of the order of 20° C., in the presence of potassium hydroxide pellets. This gives a product (12.9 g) melting at 220° C. This product, combined with a product originating from a previous operation (1.3 g), is dissolved in boiling ethanol (800 cc). The solution obtained is treated with decolourising charcoal (0.5 g) and filtered hot; the filtrate is cooled at a temperature of the order of 4° C. for 1 hour. The crystals which have appeared are filtered off, washed 3 times with ethanol cooled to a temperature of the order of 4° C. (60 cc in total) and then 3 times with diethyl ether (60 cc in total) and dried under reduced pressure (20 mm Hg; 2.7 kPa) at a temperature of the order of 20° C., in the presence of potassium hydroxide pellets. This gives 6-(pyridin-3-yl)-1,2-dihydro-4H-pyrrolo[1,2-c]-thiazine-8-carboxamide (12.6 g) in the form of white crystals melting at 220° C.

The 2-chloroacrylamide can be prepared according to S. S. IVANOV and M. M. KOTON, J. Gen. Chem. U.S.S.R., 28, 139 (1958); Chem. Abstr. 52, 12757 d, (1958).

The N-nicotinoyl-3,4,5,6-tetrahydro-2H-1,3-thiazine-4-carboxylic acid can be prepared in the following manner:

A solution of ethyl N-nicotinoyl-3,4,5,6-tetrahydro-2H-1,3-thiazine-4-carboxylate (37.8 g) in a mixture of a 5N aqueous solution of sodium hydroxide (80 cc) and ethanol (80 cc) is stirred at a temperature of the order of 20° C. for 16 hours. The solvent is then evaporated off under reduced pressure (20 mm Hg; 2.7 kPa) at a temperature of the order of 50° C. The residue is dissolved in distilled water (100 cc) and purified by passing the solution obtained over DOWEX 50WX-2 resin (50–100 mesh) (630 g) contained in a column of diameter 4.5 cm. Elution is carried out with distilled water (4,000 cc), then with a mixture of water and methanol (50/50 by volume) (1,000 cc), then with methanol (2,000 cc) and then with distilled water (2,000 cc). All the corresponding fractions are discarded. The next 6 fractions, each of 1,000 cc, from elution with a 2% strength (v/v) aqueous solution of pyridine are combined and concentrated to dryness under reduced pressure (20 mm Hg; 2.7 kPa) at a temperature of the order of 50° C. The residue is taken up in ethanol (150 cc) and the solvent is evaporated off under reduced pressure (20 mm Hg; 2.7 kPa) at a temperature of the order of 50° C. This operation is repeated once. The residue finally collected is dissolved in a boiling mixture of ethanol and water (60/40 by volume) (350 cc). The solution obtained is treated with decolourising charcoal (0.5 g) and filtered hot; the filtrate is cooled at a temperature of the order of 4° C. for 1 hour. The crystals which have appeared are filtered off, washed 3 times with a mixture of ethanol and water (60/40 by volume) (60 cc in total) and then 3 times with ethanol (60 cc in total) and dried under reduced pressure (20 mm Hg; 2.7 kPa) at a temperature of the order of 20° C., in the presence of potassium hydroxide pellets. This gives N-nicotinoyl-3,4,5,6-tetrahydro-2H-1,3-thiazine-4-carboxylic acid (24.2 g) in the form of white crystals melting at 214° C.

The ethyl N-nicotinoyl-3,4,5,6-tetrahydro-2H-1,3-thiazine-4-carboxylate can be prepared in the following manner:

A mixture of triethylamine (75 g) and chloroform (100 cc) is added in the course of 15 minutes, at a temperature of the order of 20° C., to a suspension of ethyl 3,4,5,6-tetrahydro-2H-1,3-thiazine-4-carboxylate hydrochloride (37.2 g) in chloroform (350 cc). Nicotinoyl chloride hydrochloride (50.4 g) is added to the solution thus obtained in the course of 10 minutes, at a temperature of the order of 20° C. The reaction mixture is heated at a temperature of the order of 65° C. for 1 hour 45 minutes and is then stirred at a temperature of the order of 20° C. for 16 hours. The reaction mixture is washed 3 times with distilled water (600 cc in total) and then 3 times with a saturated aqueous solution of potassium bicarbonate (600 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a product (52 g). This product is chromatographed on a column of diameter 5.2 cm, containing silica (0.063–0.2 mm) (520 g), 500 cc fractions being collected. The first fraction from elution with a mixture of cyclohexane and ethyl acetate (50/50 by volume) is discarded. The next 3 fractions from elution with a mixture of ethyl acetate and cyclohexane (50/50 by volume), the next 2 fractions from elution with a mixture of ethyl acetate and cyclohexane (70/30 by volume) and the next fraction from elution with a mixture of ethyl acetate and cyclohexane (80 20 by volume) are combined and concentrated to dryness under reduced pressure (20 mm Hg; 2.7 kPa) at a temperature of the order of 50° C. This gives ethyl N-nicotinoyl-3,4,5,6-tetrahydro-2H-1,3-thiazine-4-carboxylate (37.8 g) in the form of a yellow oil. [Rf=0.33; chromatography on a thin layer of silica gel; solvent: ethyl acetate cyclohexane (80/20 by volume)].

The ethyl 3,4,5,6-tetrahydro-2H-1,3-thiazine-4-carboxylate hydrochloride can be prepared in the following manner:

A suspension of 3,4,5,6-tetrahydro-2H-1,3-thiazine-4-carboxylic acid (47.7 g) in ethanol (650 cc) is saturated for 4 hours, at a temperature of the order of 20° C., with a stream of dry hydrogen chloride. The suspension is stirred for 3 days at a temperature of the order of 20° C. and is then heated at a temperature of the order of 80° C. for 3 hours 20 minutes, with stirring. After cooling the solution obtained to a temperature of the order of 4° C., the crystals which have appeared are filtered off, washed 3 times with ethanol cooled to a temperature of the order of 4° C. (30 cc in total) and then 3 times with diethyl ether (120 cc in total) and dried under reduced pressure (20 mm Hg; 2.7 kPa) at a temperature of the order of 20° C., in the presence of potassium hydroxide pellets. This gives ethyl 3,4,5,6-tetrahydro-2H-1,3-thiazine-4-carboxylate hydrochloride (37.2 g) in the form of white crystals melting at 185° C.

The 3,4,5,6-tetrahydro-2H-1,3-thiazine-4-carboxylic acid can be prepared according to J. C. WRISTON Jr. and C. G. MACKENZIE, J. Biol. Chem., 225, 607 (1957).

EXAMPLE 14

A suspension of powdered potassium hydroxide (11.2 g) and a mixture (in the ratio 69/31) of 6-cyano and 7-cyano-5-[2-(pyridin-3-yl)-vinyl]-1H,3H-pyrrolo[1,2-c]thiazole (10.2 g) in tert.-butyl alcohol (110 cc) is heated under reflux for one hour. The solvent is then evaporated off under reduced pressure (20 mm Hg; 2.7 kPa) at a temperature of the order of 50° C. After the addition of distilled water (200 cc), the crystals which have appeared are filtered off, washed four times with distilled water (120 cc in total) and dried under reduced pressure (20 mm Hg; 2.7 kPa) at a temperature of the order of 20° C., in the presence of potassium hydroxide pellets. This gives a crude product (11 g). This product is chromatographed on a column of diameter of 3.2 cm, containing silica (0.063–0.2 mm) (110 g), 1,000 cc fractions being collected. The first fraction from elution with pure methylene chloride, the second fraction from elution with a mixture of methylene chloride and methanol (97.5/2.5 by volume), the third fraction from elution with a mixture of methylene chloride and methanol (95/5 by volume) and the fourth fraction from elution with a mixture of methylene chloride and methanol (92.5/7.5 by volume) are discarded. The fifth fraction from elution with a mixture of methylene chloride and methanol (90/10 by volume) and the sixth fraction from elution with a mixture of methylene chloride and methanol (85/15 by volume) are combined and concentrated to dryness under reduced pressure (20 mm Hg; 2.7 kPa) at a temperature of the order of 40° C. This gives a product (3.7 g) melting at 180° C. This product is dissolved in boiling acetonitrile (700 cc). After cooling at a temperature of the order of 4° C. for one hour, the crystals which have appeared are filtered off and dried and reduced pressure (20 mm Hg; 2.7 kPa) at a temperature of the order of 20° C., in the presence of potassium hydroxide pellets. This gives a product (2.4 g), which is combined with a product prepared in the same way in a previous operation (0.9 g) and chromatographed on a column of diameter 2.8 cm, containing silica (0.063–0.2 mm) (35 g), 500 cc fractions being collected. The first two fractions from elution with pure methylene chloride and the next two from elution with a mixture of methylene chloride and methanol (97.5/2.5 by volume) are discarded. The fifth and sixth fractions from elution with a mixture of methylene chloride and methanol (95/5 by volume) and the seventh fraction from elution with a mixture of methylene chloride and methanol (90/10 by volume) are combined and concentrated to dryness under reduced pressure (20 mm Hg; 2.7 kPa) at a temperature of the order of 40° C. This gives a product (3.1 g), which is dissolved in boiling acetonitrile (900 cc). The solution is treated with decolourising charcoal (0.3 g) and filtered hot. After cooling at a temperature of the order of 4° C. for 2 hours, the crystals which have appeared are filtered off, washed twice with acetonitrile (60 cc in total) and dried under reduced pressure (20 mm Hg; 2.7 kPa) at a temperature of the order of 20° C., in the presence of potassium hydroxide pellets. This gives 5-[2-(pyridin-3-yl)-vinyl]-1H,3H-pyrrolo[1,2-c]thiazole-7-carboxamide (2.1 g) melting at 242° C.

The mixture (69/31) of 6-cyano and 7-cyano-5-[2-(pyridin-3-yl)vinyl]-1H,3H-pyrrolo[1,2-c]thiazole can be prepared in the following manner:

A suspension of N-[3-(pyridin-3-yl)-acryloyl]-thiazolidine-4-carboxylic acid (13.2 g) in a mixture of 2-chloroacrylonitrile (39.6 cc) and acetic anhydride (52 cc) is heated at about 83° C. for 4 hours. After cooling for 16 hours at a temperature of the order of 4° C., the crystals which have appeared are filtered off and washed twice with acetic anhydride (10 cc in total) and three times with aceto e (60 cc in total). The product thus obtained is suspended in distilled water (70 cc). The mixture is brought to a pH of the order of 10 by adding a 2N aqueous solution of sodium hydroxide. After stirring at a temperature of the order of 20° C. for one hour, the crystals which have appeared are filtered off, washed three times with distilled water (60 cc in total), twice with acetone (40 cc in total) and twice with diethyl ether (40 cc in total) and dried under reduced pressure (20 mm Hg; 2.7 kPa) at a temperature of the order of 20° C., in the presence of potassium hydroxide pellets. This gives a mixture of 6-cyano and 7-cyano-5-[2-(pyridin-3-yl)-vinyl]-1H,3H-pyrrolo[1,2-c]thiazole in the form of beige crystals melting at 170° C.

The N-[3-(pyridin-3-yl)-acryloyl]-thiazolidine-4-carboxylic acid can be obtained in the following manner:

3-(Pyridin-3-yl)-acryloyl chloride hydrochloride (34.1 g) is added in the course of 30 minutes, at a temperature of between 20° C. and 35° C., to a solution of thiazolidine-4-carboxylic acid (22.5 g) in a mixture of triethylamine (47 cc) and chloroform (250 cc). The reaction mixture is heated under reflux for 16 hours and then concentrated to dryness under reduced pressure (20 mm Hg; 2.7 kPa). The residue obtained, treated with distilled water (500 cc), is heated to the reflux temperature. After the addition of decolourising charcoal (1 g), the mixture is filtered hot and the filtrate is cooled at 4° C. for 16 hours. The crystals which have appeared are filtered off, washed twice with distilled water (100 cc in total) and once with ethanol (30 cc) and dried under reduced pressure (20 mm Hg; 2.7 kPa) at a temperature of the order of 20° C., in the presence of potassium hydroxide pellets. This gives a crude product (21.1 g) melting at 173° C. This product is dissolved in boiling ethanol (400 cc). The solution obtained is treated with decolourising charcoal (1 g) and filtered hot. The filtrate is cooled at a temperature of the order of 4° C. for 16 hours. The crystals which have appeared are filtered off, washed twice with ethanol (40 cc) in total and dried under reduced pressure (20 mm Hg; 2.7 kPa) at a temperature of the order of 20° C., in the presence of potassium hydroxide pellets. This gives N-[3-(pyridin-3-yl)-acryloyl]-thiazolidine-4-carboxylic acid (13.5 g) melting at 176° C.

The 3-(pyridin-3-yl)-acryloyl chloride hydrochloride can be obtained in the following manner:

Thionyl chloride (200 cc) is added in the course of 15 minutes to 3-(pyridin-3-yl)-acrylic acid (50 g). The reaction mixture is then heated under reflux for 5 hours. The excess thionyl chloride is distilled and the reaction mixture is then concentrated to dryness after the addition of anhydrous cyclohexane (300 cc). This last operation is repeated once. The residue obtained is treated with chloroform (200 cc) and the mixture is heated under reflux for 15 minutes. After cooling, the crystals are filtered off, washed once with chloroform (50 cc) and twice with hexane (200 cc in total) and then dried under reduced pressure (20 mm Hg; 2.7 kPa) at a temperature of the order of 20° C., in the presence of potassium hydroxide pellets. This gives 3-(pyridin-3-yl)acryloyl chloride hydrochloride (55 g) melting at 187° C.

The 3-(pyridin-3-yl)-acrylic acid can be prepared according to L. PANNIZZON, Helv. Chim. Acta, 24, 24E (1941).

EXAMPLE 15

A solution of morpholine (10.45 g) in methylene chloride (50 cc) is added in the course of 15 minutes, at a temperature of between 24° C. and 33° C., to a suspension of 7-chloroformyl-5-(pyridin-3-yl)-1H,3H-pyrrolo[1,2-c]thiazole hydrochloride (12 g) in methylene chloride (200 cc). The solution obtained is stirred at a temperature of the order of 20° C. for 16 hours and is then diluted with methylene chloride (250 cc), washed twice with distilled water (400 cc in total), once with a 2N aqueous solution of sodium hydroxide (200 cc) and then twice with distilled water (400 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (12.7 g). The product is dissolved in boiling acetonitrile (125 cc). The solution obtained is treated with decolourising charcoal (0.5 g) and filtered hot. The filtrate is cooled at a temperature of the order of 4° C. for 2 hours. The crystals which have appeared are filtered off, washed twice with acetonitrile cooled to a temperature of the order of 4° C. (10 cc in total) and 3 times with isopropyl ether (75 cc in total) and then dried under reduced pressure (20 mm Hg; 2.7 kPa) at a temperature of the order of 20° C., in the presence of potassium hydroxide pellets. This gives 7-morpholinocarbonyl-5-(pyridin-3-yl)-1H,3H-pyrrolo[1,2-c]thiazole (7.5 g) in the form of beige crystals melting at 150° C.

The 7-chloroformyl-5-(pyridin-3-yl)-1H,3H-pyrrolo[1,2-c]thiazole hydrochloride is prepared as in Example 3.

EXAMPLE 16

A solution of 7-chloroformyl-5-(pyridin-3-yl)-1H,3H-pyrrolo[1,2-c]thiazole hydrochloride (30 g) and triethylamine (20.2 g) in methylene chloride (500 cc) is added in the course of 25 minutes at a temperature of between 24° C. and 32° C., to a solution of anhydrous piperazine (26.1 g) in methylene chloride (500 cc). The suspension obtained is stirred at a temperature of the order of 20° C. for 16 hours and is then diluted with methylene chloride (600 cc) and washed twice with a 2N aqueous solution of sodium hydroxide (600 cc in total). The organic phase is decanted, washed 3 times with distilled water (1,550 cc in total), dried over anhydrous magnesium sulphate, treated with decolourising charcoal (1 g) and filtered, and the filtrate is concentrated to dryness under reduced pressure (20 mm Hg; 2.7 kPa) at a temperature of the order of 60° C. This gives a product (25.4 g). This product is dissolved in boiling butan-1-ol (160 cc). The solution obtained is treated with decolourising charcoal (0.5 g) and filtered hot. The filtrate is cooled at a temperature of the order of 4° C. for 16 hours. The crystals which have appeared are filtered off and the filtrate is concentrated to dryness under reduced pressure (20 mm Hg; 2.7 kPa) at a temperature of the order of 70° C. This gives a product (21 g), which is chromatographed on a column of diameter of 3.8 cm, containing silica (0.063–0.2 mm) (210 g). Elution is carried out with mixtures of methylene chloride and methanol, 300 cc fractions being collected. The first 7 fractions from elution with a mixture of methylene chloride and methanol (95/5 by volume) are discarded; the next 3 fractions from elution with a mixture of methylene chloride and methanol (95/5 by volume), the next 7 fractions from elution with a mixture of methylene chloride and methanol (90/10 by volume) and the next 8 fractions from elution with a mixture of methylene chloride and methanol (85/15 by volume) are combined and concentrated to dryness under reduced pressure (20 mm Hg; 2.7 kPa) at a temperature of the order of 60° C. This gives a product (12.2 g). This product is suspended in distilled water (50 cc) and the suspension obtained is treated with 5N aqueous solution of sodium hydroxide (100 cc) and extracted 3 times with methylene chloride (750 cc in total). The organic extracts are combined, washed twice with distilled water (200 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a product (11 g). This product is taken up in boiling methanol (30 cc). The suspension obtained is filtered hot in the presence of decolourising charcoal (0.5 g) and the filtrate is cooled at a temperature of the order of 4° C. for 3 hours. The crystals which have appeared are filtered off, washed twice with methanol cooled to a temperature of the order of 4° C. (10 cc in total) and 3 times with diethyl ether (75 cc in total) and then dried under reduced pressure (20 mm Hg; 2.7 kPa) at a temperature of the order of 20° C., in the presence of potassium hydroxide pellets. This gives a product (5.9 g) melting at 252° C. The mother liquors are concentrated to dryness under reduced pressure (20 mm Hg; 2.7 kPa) at a temperature of the order of 60° C. This gives a product (2.8 g), which is taken up in ethanol (25 cc). The suspension obtained is heated at the boil for 5 minutes and then cooled to a temperature of the order of 20° C. The crystals are filtered off, washed twice with ethanol (10 cc in total) and dried under reduced pressure (20 mm Hg; 2.7 kPa) at a temperature of the order of 20° C., in the presence of potassium hydroxide pellets. This gives a product (0.3 g) melting at 262° C. The filtrate is poured into a 0.64N ethanolic solution of hydrogen chloride (28 cc). The crystals which have appeared are filtered off, washed twice with ethanol (20 cc in total) and 3 times with isopropyl ether (75 cc in total) and then dried under reduced pressure (20 mm Hg; 2.7 kPa) at a temperature of the order of 20° C., in the presence of potassium hydroxide pellets. This gives a crude product (2.5 g) melting at 260° C. This product, combined with the products obtained previously (0.3 g and 5.9 g), is suspended in a 5.35N ethanolic solution of hydrogen chloride (600 cc). After stirring for 35 minutes at a temperature of the order of 20° C., dissolution is observed, followed by crystallisation 10 minutes later. The suspension obtained is stirred at a temperature of the order of 20° C. for 16 hours. The crystals are filtered off, washed 3 times with ethanol (75 cc in total) and 3 times with diethyl ether (75 cc in total) and then dried under reduced pressure (20 mm Hg; 2.7 kPa) at a temperature of the order of 20° C., in the presence of potassium hydroxide pellets. This gives 7-(piperazin-1-yl-carbonyl)-5-(pyridin-3-yl)-1H,3H-pyrrolo[1,2-c]thiazole as the trihydrochloride monohydrate (6.7 g) in the form of pale yellow crystals melting at 242° C.

The 5-(pyridin-3-yl)-1H,3H-pyrrolo[1,2-c]thiazole-7-carboxylic acid is prepared as in Example 3.

EXAMPLE 17

A solution of 1-(2-aminoethyl)-4-methylpiperazine (3.7 g) and triethylamine (5.3 g) in methylene chloride (45 cc) is added in the course of 20 minutes, at a temperature of between 21° C. and 31° C., to a suspension of 7-chloroformyl-5-(pyridin-3-yl)-1H,3H-pyrrolo[1,2-c]thiazole hydrochloride (7.8 g) in methylene chloride (130 cc). The solution obtained is stirred at a temperature of the order of 20° C. for 16 hours and is then diluted with methylene chloride (200 cc), washed 4 times with distilled water (800 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a product (6.3 g). This product is dissolved in distilled water (150 cc). The solution obtained and the previous wash waters are combined and rendered alkaline by adding a 5N aqueous solution of sodium hydroxide (250 cc). The suspension obtained is extracted 3 times with methylene chloride (750 cc in total). The organic extracts are combined, washed 3 times with distilled water (750 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (7.6 g). This product is dissolved in ethanol (150 cc) and the solution obtained is added in the course of 15 minutes, at a temperature of the order of 20° C., to a 1.26N ethanolic solution of hydrogen chloride (65 cc). The suspension obtained is treated with ethanol (25 cc) and then stirred at a temperature of the order of 20° C. for 2 hours. The crystals are filtered off, washed 3 times with ethanol (75 cc in total) and 4 times with diethyl ether (100 cc in total) and then dried under reduced pressure (20 mm Hg; 2.7 kPa) at a temperature of the order of 20° C., in the presence of potassium hydroxide pellets. This gives N-[2-(4-methylpiperazin-1-yl)-ethyl]-5(pyridin-3-yl)-1H,3H-pyrrolo[1,2-c]thiazole-7-carboxamide as the trihydrochloride (7.4 g) in the form of pale yellow crystals melting at 260° C.

The 7-chloroformyl-5-(pyridin-3-yl)-1H,3H-pyrrolo[1,2-c]thiazole hydrochloride is prepared as in Example 3.

EXAMPLE 18

7-Chloroformyl-5-(pyridin-3-yl)-1H,3H-pyrrolo[1,2-c]thiazole hydrochloride (12 g) is added in the course of 35 minutes, at a temperature of between 23° C. and 30° C., to a solution of 4-(2-hydroxyethyl)-piperazine (5.3 g) and triethylamine (8.1 g) in methylene chloride (250 cc). The solution obtained is stirred at a temperature of the order of 20° C. for 16 hours and is then diluted with methylene chloride (200 cc) and washed 4 times with distilled water (800 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (14 g). This product is dissolved in boiling ethanol (130 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol (50 cc in total) and 4 times with isopropyl ether (100 cc in total) and then dried under reduced pressure (20 mm Hg; 2.7 kPa) at a temperature of the order of 20° C., in the presence of potassium hydroxide pellets. This gives 7-[4-(2-hydroxyethyl)-piperazin-1-yl]-carbonyl-5-(pyridin-3-yl)-1H,3H-pyrrolo[1,2-c]thiazole (8.3 g) in the form of cream crystals melting at 140° C.

The 7-chloroformyl-5-(pyridin-3-yl)-1H,3H-pyrrolo[1,2-c]thiazole hydrochloride is prepared as described in Example 3.

EXAMPLE 19

A solution of 1-benzylpiperazine (30.6 g) in methylene chloride (150 cc) is added in the course of 30 minutes, at a temperature of between 24° C. and 31° C., to a suspension of 7-chloroformyl-5-(pyridin-3-yl)-1H,3H-pyrrolo[1,2-c]thiazole hydrochloride (15 g) in methylene chloride (300 cc). The solution obtained is stirred at a temperature of the order of 20° C. for 16 hours and then diluted with methylene chloride (300 cc), washed 3 times with distilled water (750 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (22.7 g). This product is dissolved in boiling acetonitrile (100 cc). The solution obtained is treated with decolourising charcoal (0.5 g) and filtered hot. The filtrate is cooled at a temperature of the order of 4° C. for 1 hour. The crystals which have appeared are filtered off, washed twice with acetonitrile cooled to a temperature of the order of 4° C. (50 cc in total) and 3 times with diethyl ether (75 cc in total) and then dried under reduced pressure (20 mm Hg; 2.7 kPa) at a temperature of the order of 20° C., in the presence of potassium hydroxide pellets. This gives 7-[(4-benzylpiperazin-1-yl)-carbonyl]-5-(pyridin-3-yl)-1H,3H-pyrrolo[1,2-c]thiazole (13 g) in the form of cream crystals melting at 140° C.

The 7-chloroformyl-5-(pyridin-3-yl)-1H,3H-pyrrolo[1,2-c]thiazole hydrochloride is prepared as described in Example 3.

EXAMPLE 20

A solution of 1-[(pyrrolidin-1-yl)-carbonylmethyl]-piperazine (10.2 g) and triethylamine (10.1 g) in methylene chloride (100 cc) is added in the course of 30 minutes, at a temperature of between 24° and 32° C., to a suspension of 7-chloroformyl-5-(pyridin-3-yl)-1H,3H-pyrrolo[1,2-c]thiazole hydrochloride (15 g) in methylene chloride (250 cc). The solution obtained is stirred at a temperature of the order of 20° C. for 16 hours and is then diluted with methylene chloride (300 cc), washed 3 times with distilled water (900 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (20.8 g). This product is taken up in acetonitrile (80 cc). A product crystallises. The suspension obtained is heated to the boil and the solution obtained is then treated with decolourising charcoal (0.5 g) and filtered hot. The filtrate is cooled at a temperature of the order of 4° C. for 16 hours. The crystals which have appeared are filtered off, washed twice with acetonitrile cooled to a temperature of the order of 4° C. (20 cc in total) and 4 times with diethyl ether (200 cc in total) and then dried under reduced pressure (20 mm Hg; 2.7 kPa) at a temperature of the order of 20° C., in the presence of potassium hydroxide pellets. This gives 7-[(4-pyrrolidin-1-yl-carbonylmethylpiperazin-1-yl)-carbonyl]-5-(pyridin-3-yl)-1H,3H-pyrrolo[1,2-c]thiazole (13.2 g) in the form of beige crystals melting at 164° C.

The 7-chloroformyl-5-(pyridin-3-yl)-1H,3H-pyrrolo[1,2-c]thiazole hydrochloride is prepared as in Example 3.

EXAMPLE 21

7-Chloroformyl-5-(pyridin-3-yl)-1H,3H-pyrrolo[1,2-c]thiazole hydrochloride (17.5 g) is added in the course of 15 minutes, at a temperature of between 18° and 27° C., to a solution of histamine (12.9 g) in methylene chloride (360 cc). The suspension obtained is stirred at a temperature of the order of 20° C. for 16 hours and is then treated with a mixture of methylene chloride (360 cc) and water (300 cc). The crystals which have appeared are filtered off, washed 3 times with methylene chloride (30 cc in total), 3 times with distilled water (300 cc in total), 3 times with a 2N aqueous solution of sodium hydroxide (300 cc in total) and 3 times with distilled water (300 cc in total) and dissolved in a 2N aqueous solution of hydrochloric acid (100 cc). The solutin obtained is treated with decolourising charcoal (0.5 g) and filtered. The filtrate is brought to a pH of the order of 10 by adding a 10N aqueous solution of sodium hydroxide. The crystals which have appeared are filtered off, washed 3 times with distilled water (150 cc in total) and 3 times with acetone (75 cc in total) and dried under reduced pressure (20 mm Hg; 2.7 kPa) at a temperature of the order of 20° C., in the presence of potassium hydroxide pellets. This gives a crude product (11.8 g). This product is dissolved in boiling isopropanol (250 cc). The solution obtained is treated with decolourising charcoal (0.5 g) and filtered hot. The filtrate is cooled at a temperature of the 4° C. for 16 hours. The pasty precipitate which has appeared is filtered off and the filtrate is concentrated to dryness under reduced pressure (20 mm Hg; 2.7 kPa) at a temperature of the order of 60° C. This gives a product (8.4 g) melting at 200° C. This product is dissolved in boiling ethanol (350 cc). The solution obtained is treated with decolourising charcoal (0.5 g) and filtered hot. The filtrate is cooled for 16 hours at a temperature of the order of 20° C. The crystals which have appeared are filtered off, washed 3 times with ethanol (30 cc in total) and 3 times with diethyl ether (75 cc in total) and dried under reduced pressure (20 mm Hg; 2.7 kPa) at a temperature of the order of 20° C., in the presence of potassium hydroxide pellets. This gives N-[2-(imidazol-4-yl)ethyl]-5-(pyridin-3-yl)-1H,3H-pyrrolo[1,2-c]thiazole-7-carboxamide (5.6 g) in the form of cream crystals melting at 226° C.

The 7-chloroformyl-5-(pyridin-3-yl)-1H,3H-pyrrolo[1,2-c]thiazole hydrochloride is prepared as described in Example 3.

EXAMPLE 22

A suspension of 5-(pyridin-3-yl)-1H,3H-pyrrolo[1,2-c]thiazole-7-carbonitrile (3.6 g), ethanolamine (3.8 g) and lithium chloride (0.1 g) is heated at a temperature of the order of 122° C. for 22 hours. Ethanolamine (1.9 g) and lithium chloride (0.1 g) are then added to the reaction mixture and heating is continued for a further 26 hours. After the reaction mixture has cooled to a temperature of the order of 20° C., solidification is observed. Ethanol (25 cc) is then added in order to break up the crystals. After stirring for 30 minutes at a temperature of the order of 20° C., the crystals are filtered off, washed twice with ethanol (10 cc in total) and 3 times with isopropyl ether (75 cc in total) and then dried under reduced pressure (20 mm Hg; 2.7 kPa) at a temperature of the order of 20° C., in the presence of potassium hydroxide pellets. This gives a crude product (3.1 g) melting at 150° C. This product is dissolved in boiling ethanol (40 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol (10 cc in total) and 3 times with isopropyl ether (45 cc) in total and then dried under reduced pressure (20 mm Hg; 2.7 kPa) at a temperature of the order of 20° C., in the presence of potassium hydroxide pellets. This gives N-[2-(2-hydroxyethyl)-aminoethyl]-5-(pyridin-3-yl)-1H,3H-pyrrolo[1,2-c]thiazole-7-carboxamide (2 g) in the form of pale yellow crystals melting at 163° C.

The 5-(pyridin-3-yl)-1H,3H-pyrrolo[1,2-c]thiazole-7-carbonitrile is prepared as in Example 1.

EXAMPLE 23

A suspension of powdered potassium hydroxide (12.3 g) and a mixture (in the ratio 20/80) of 6-cyano- and 7-cyano-3-phenyl-5-(pyridin-3-yl)-1H,3H-pyrrolo[1,2-c]thiazole (11.3 g) in tert.-butyl alcohol (260 cc) is heated under reflux for 3 hours. The suspension is stirred for 16 hours at a temperature of the order of 20° C. and is then concentrated to dryness under reduced pressure (20 mm Hg; 2.7 kPa) at a temperature of the order of 60° C. The residue obtained is suspended in distilled water (300 cc) and is extracted 3 times with ethyl acetate (750 cc in total). The organic extracts are combined, washed 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (9.2 g). This product is chromatographed on a column of diameter 6 cm, containing silica (0.04–0.063 mm) (480 g). Elution is carried out with a mixture of ethyl acetate and methanol (95/5 by volume) under a pressure of 0.5 bar (51 kPa), 200 cc fractions being collected. The first 10 fractions are discarded. The next 12 fractions are combined and concentrated to dryness under reduced pressure (20 mm Hg; 2.7 kPa) at a temperature of the order of 60° C. This gives a product (7 g). This product is dissolved in ethanol (140 cc). The solution obtained is treated with a 2N ethanolic solution of hydrogen chloride (3.1 cc) and stirred at a temperature of the order of 20° C. for 15 minutes. The crystals which have appeared are filtered off, washed twice with ethanol (50 cc in total) and 3 times with diethyl ether (75 cc in total) and dried under reduced pressure (20 mm Hg; 2.7 kPa) at a temperature of the order of 20° C., in the presence of potassium hydroxide pellets. This gives 3-phenyl-5-(pyridin-3-yl)-1H,3H-pyrrolo[1,2-c]thiazole-7-carboxamide hydrochloride (6 g) in the form of yellow crystals melting at 250° C.

The mixture (20/80) of 6-cyano and 7-cyano-3-phenyl-5-(pyridin-3-yl)-1H,3H-pyrrolo[1,2-c]thiazole can be prepared in the following manner:

A suspension of N-nicotinoyl-2-phenylthiazolidine-4-carboxylic acid (45.2 g) in a mixture of 2-chloroacrylonitrile (115 cc) and acetic anhydride (180 cc) is heated at a temperature of the order of 90° C. for 3 hours and the solution obtained is stirred at a temperature of the order of 20° C. for 16 hours. The solvent is evaporated off under reduced pressure (20 mm Hg; 2.7 kPa) at a temperature of the order of 60° C. and the residue is taken up at a temperature of the order of 4° C. in a mixture of distilled water (300 cc), a 10N aqueous solution of sodium hydroxide (400 cc) and ethyl acetate (500 cc). The organic phase is separated off by decantation and the aqueous phase is extracted 3 times with ethyl acetate (1,500 cc in total) and 4 times with methylene chloride (2,000 cc in total). The organic extracts are combined, washed 4 times with distilled water (1,000 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (33.8 g). This product is chromatographed on a column of diameter 6 cm, containing silica (0.04–0.063 mm) (480 g). Elution is carried out with a mixture of cyclohexane and ethyl acetate (50/50 by volume) under a pressure of 0.5 bar (51 kPa), 100 cc fractions being collected. The first 17 fractions are discarded and the next 14 fractions are combined and concentrated to dryness under reduced pressure (20 mm Hg; 2.7 kPa) at a temperature of the order of 60° C. This gives a mixture of 6-cyano and 7-cyano-3 phenyl 5-(pyridin-3-yl)-1H,3H-pyrrolo[1,2-c]thiazole (11.3 g), in a ratio of 20/80 (according to the NMR spectrum), in the form of a brown oil.

[Rf=0.35 and 0.4; chromatography on a thin layer of silica gel; solvent: cyclohexane/ethyl acetate (50/50 by volume)].

The N-nicotinoyl-2-phenylthiazolidine-4-carboxylic acid can be prepared in the following manner:

Nicotinoyl chloride hydrochloride (88.1 g) is added in the course of 20 minutes, at a temperature of between 32° and 54° C., to a solution of 2-phenylthiazolidine-4-carboxylic acid (94.2 g) and triethylamine (100 g) in chloroform (1,120 cc). The solution obtained is heated at a temperature of the order of 63° C. for 5 hours and is then stirred at a temperature of the order of 20° C. for 16 hours. A product crystallises. The suspension is cooled at a temperature of the order of 4° C. for 1 hour. The crystals which have appeared are filtered off, washed 3 times with chloroform (300 cc in total) and dried under reduced pressure (20 mm Hg; 2.7 kPa) at a temperature of the order of 20° C., in the presence of potassium hydroxide pellets. This gives a crude product (145 g) melting at 150° C. This product is suspended in distilled water (750 cc). The crystals are filtered off, washed 3 times with distilled water (750 cc in total) and dried in air. This gives a product (90.9 g) melting at 182° C. This product (15 g) is dissolved in boiling ethanol (200 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol (50 cc in total) and 3 times with diethyl ether (75 cc in total) and dried under reduced pressure (20 mm Hg; 2.7 kPa) at a temperature of the order of 20° C., in the presence of potassium hydroxide pellets. This gives N-nicotinoyl-2-phenyl-thiazolidine-4-carboxylic acid (11.4 g) in the form of white crystals melting at 186° C.

The 2-phenylthiazolidine-4-carboxylic acid can be prepared according to R. RIEMSCHNEIDER and G. A. HOYER, Z. Naturforsch, 17 B, 765 (1962).

EXAMPLE 24

A suspension of powdered potassium hydroxide (20.4 g) and a mixture (in the ratio 50/50) of 6-cyano and 7-cyano-3-methyl-5-(pyridin-3-yl)-1H,3H-pyrrolo[1,2-c]thiazole (17.6 g) in tert.-butyl alcohol (200 cc) is heated under reflux for 1 hour 20 minutes. The solvent is evaporated off under reduced pressure (20 mm Hg; 2.7 kPa) at a temperature of the order of 50° C. The residue is treated with a mixture of distilled water (200 cc) and methylene chloride (100 cc). The organic phase is separated off by decantation and the aqueous phase is extracted 4 times with methylene chloride (400 cc in total). The organic extracts are combined, washed 5 times with distilled water (750 cc in total), dried over anhydrous magnesium sulphate and filtered, and the filtrate is concentrated to dryness under reduced pressure (20 mm Hg; 2.7 kPa) at a temperature of the order of 50°. This gives a product (19 g). This product is dissolved in methylene chloride (50 cc). Crystals appear; they are filtered off, washed 3 times with methylene chloride (15 cc in total) and dried under reduced pressure (20 mm Hg; 2.7 kPa), in the presence of potassium hydroxide pellets. This gives a product (6.1 g) melting at 170° C. The filtrate is chromatographed on a column of diameter 6 cm, containing silica (0.04–0.063 mm) (480 g). Elution is carried out with mixtures of ethyl acetate and methanol under a pressure of 0.5 bar (51 kPa), 250 cc fractions being collected. The first 13 fractions from elution with a mixture of ethyl acetate and methanol (97.5/2.5 by volume) are discarded. The next 3 fractions from elution with a mixture of ethyl acetate and methanol (95/5 by volume) and the next three fractions from elution with a mixture of ethyl acetate and methanol (95/5 by volume) are combined and concentrated to dryness under reduced pressure (20 mm Hg; 2.7 kPa) at a temperature of the order of 50° C. This gives a product (3.1 g), which is combined with the previously obtained product (6.1 g) and dissolved in boiling isopropanol (90 cc). The solution obtained is treated with decolourising charcoal (0.5 g) and filtered hot. The filtrate is cooled at a temperature of the order of 4° C. for 1 hour. The crystals which have appeared are filtered off, washed 3 times with isopropanol cooled to a temperature of the order of 4° C. (6 cc in total) and 3 times with diethyl ether (30 cc in total) and dried under reduced pressure (20 mm Hg; 2.7 kPa) at a temperature of the order of 20° C., in the presence of potassium hydroxide pellets. This gives 3-methyl-5-(pyridin-3-yl)-1H,3H-pyrrolo[1,2-c]thiazole-7-carboxamide (5.6 g) in the form of cream crystals melting at 170° C.

The mixture (50/50) of 6-cyano and 7-cyano-3-methyl-5-(pyridin-3-yl)-1H,3H-pyrrolo[1,2-c]thiazole can be obtained in the following manner:

A suspension of N-nicotinoyl-2-methylthiazolidine-4-carboxylic acid (36.3 g) in a mixture of 2-chloroacrylonitrile (113 cc) and acetic anhydride (200 cc) is heated at a temperature of the order of 90° C. for 3 hours. The solution obtained is concentrated to dryness under reduced pressure (20 mm Hg; 2.7 kPa) at a temperature of the order of 70° C. and the residue obtained is taken up in distilled water (200 cc). The suspension obtained is brought to a pH of the order of 10 by adding a 10N aqueous solution of sodium hydroxide (80 cc), the reaction mixture being kept at a temperature of the order of 20° C. The suspension obtained is treated with methylene chloride (250 cc) and stirred at a temperature of the order of 20° C. for 16 hours. The organic phase is separated off by decantation and the aqueous phase is extracted 5 times with methylene chloride (500 cc in total). The organic extracts are combined and washed 5 times with distilled water (500 cc in total) and 5 times with a 2N aqueous solution of hydrochloric acid (400 cc in total). The aqueous phase is separated off be decantation, treated with decolourising charcoal (0.5 g) and filtered, and the filtrate is brought to a pH of the order of 10 by adding a 10N aqueous solution of sodium hydroxide and extracted 5 times with methylene chloride (500 cc in total). The organic extracts are combined, dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (19.3 g). This product is chromatographed on a column of diameter 6 cm, containing silica (0.04–0.063 mm) (480 g). Elution is carried out with a mixture of cyclohexane and ethyl acetate (50/50 by volume) under a pressure of 0.5 bar (51 kPa), 200 cc fractions being collected. The first 8 fractions are discarded and the next 8 fractions are combined and concentrated to dryness under reduced pressure (20 mm Hg; 2.7 kPa) at a temperature of the order of 50° C. This gives a mixture of 6-cyano and 7-cyano-3-methyl-5-(pyridin-3-yl)-1H,3H-pyrrolo[1,2-c]thiazole (17.6 g), in a ratio of 50/50 (according to the NMR spectrum), in the form of a yellow oil.

[Rf=0.35 and 0.4; chromatography on a thin layer of silica gel; solvent: cyclohexane/ethyl acetate (50/50 by volume)].

The N-nicotinoyl-2-methylthiazolidine-4-carboxylic acid can be prepared in the following manner:

Nicotinoyl chloride hydrochloride (53.4 g) is added in the course of 25 minutes, at a temperature of between 20° C. and 47° C., to a suspension of 2-methylthiazolidine-4-carboxylic acid (44.1 g) and triethylamine (61.8 g) in chloroform (500 cc). The suspension obtained is heated at a temperature of the order of 65° C. for 1 hour 45 minutes and the solution obtained is then stirred at a temperature of the order of 20° C. for 16 hours. The solvent is evaporated off under reduced pressure (20 mm Hg; 2.7 kPa) at a temperature of the order of 50° C. and the residue obtained is suspended in acetone (300 cc). After stirring for 2 hours at a temperature of the order of 20° C., the crystals which have appeared are filtered off, washed twice with acetone (400 cc in total) and dried under reduced pressure (20 mm Hg; 2.7 kPa) at a temperature of the order of 20° C., in the presence of potassium hydroxide pellets. The solid obtained is suspended in distilled water (250 cc) and the crystals which have appeared are filtered off, washed 3 times with distilled water (450 cc in total) and 3 times with acetone (60 cc in total) and dried under reduced pressure (20 mm Hg; 2.7 kPa) at a temperature of the order of 20° C., in the presence of potassium hydroxide pellets. This gives N-nicotinoyl-2-methylthiazolidine-4-carboxylic acid (36.5 g) in the form of cream crystals melting at 190° C.

The 2-methylthiazolidine-4-carboxylic acid can be prepared according to H. T. NAGASAWA, D. J. W. GOON, R. T. ZERA and D. L. YUZON, J. Med. Chem., 25, 489 (1982).

EXAMPLE 25

Triethylamine (50.1 g) is added in the course of 15 minutes, at a temperature of the order of 10° C., to a suspension of 2-aminoethanethiol hydrochloride (51.1 g) in ethanol (250 cc). The suspension obtained is stirred at a temperature of the order of 10° C. for 15 minutes and then filtered. The filtrate is treated with 5-(pyridin-3-yl)-1H,3H-pyrrolo[1,2-c]thiazole-7-carbonitrile (20.5 g) and the suspension obtained is heated at the boil for 22 hours. The solution obtained is cooled to a temperature of the order of 4° C. and the crystals which have appeared are filtered off, washed 3 times with ethanol cooled to a temperature of the order of 4° C. (75 cc in total) and 4 times with diethyl ether (100 cc in total) and then dried under reduced pressure (20 mm Hg; 2.7 kPa) at a temperature of the order of 20° C., in the presence of potassium hydroxide pellets. This gives a product (25 g) melting at 136° C. This product is combined with the product originating from another earlier operation (1.5 g) and dissolved in boiling ethanol (400 cc). The solution obtained is treated with decolourising charcoal (0.5 g) and filtered hot. The filtrate is cooled at a temperature of the order of 4° C. for 1 hour. The crystals which have appeared are filtered off, washed 3 times with ethanol (75 cc in total) and 3 times with diethyl ether (150 cc in total) and dried under reduced pressure (20 mm Hg; 2.7 kPa) at a temperature of the order of 20° C., in the presence of potassium hydroxide pellets. This gives a product (23 g) melting at 124° C. This product is dissolved in boiling acetonitrile (300 cc). The solution obtained is treated with decolourising charcoal (0.5 g) and filtered hot. The filtrate is cooled at a temperature of the order of 4° C. for 1 hour. The crystals which have appeared are filtered off, washed 3 times with acetonitrile cooled to a temperature of the order of 4° C. (75 cc in total) and 3 times with diethyl ether (150 cc in total) and then dried under reduced pressure (20 mm Hg; 2.7 kPa) at a temperature of the order of 20° C., in the presence of potassium hydroxide pellets. This gives 7-(4,5-dihydrothiazol-2-yl)-5-(pyridin-3-yl)-1H,3H-pyrrolo[1,2-c]thiazole (20.1 g) in the form of orange-yellow crystals melting at 124° C.

The 5-(pyridin-3-yl)-1H,3H-pyrrolo[1,2-c]thiazole-7-carbonitrile is prepared as in Example 1.

EXAMPLE 26

A suspension of methyl 5-(pyridin-3-yl)-1H,3H-pyrrolo[1,2-c]thiazole-7-carbodithioate (24.85 g), ethylenediamine (15.6 g) and mercuric chloride (23.1 g) is heated at a temperature of the order of 78° C. for 3 hours. Mercuric chloride (23.1 g) is then added to the suspension and heating is continued for a further 17 hours. The suspension is then cooled to a temperature of the order of 20° C. and the solvent is evaporated off under reduced pressure (20 mm Hg; 2.7 kPa) at a temperature of the order of 60° C. The residue is suspended in water (850 cc) at a temperature of the order of 85° C. A 10N aqueous solution of sodium hydroxide (1,200 cc) is added to this suspension and heating is continued at a temperature of the order of 85° C. for 1 hour, with stirring. The suspension is then cooled to a temperature of the order of 20° C. and the crystals are filtered off and washed 4 times with distilled water (1,000 cc in total). The crystals thus obtained are suspended in boiling chloroform (1,000 cc) and the suspension is filtered hot. The same operation is repeated twice. The filtrates are combined, dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (18.4 g) melting at 184° C. This product is dissolved in boiling isopropanol (200 cc). The solution obtained is treated with decolourising charcoal (0.5 g) and filtered hot. The filtrate is cooled at a temperature of the order of 4° C. for 3 days. The crystals which have appeared are filtered off, washed twice with isopropanol (30 cc in total) and 3 times with diethyl ether (75 cc in total) and then dried under reduced pressure (20 mm Hg; 2.7 kPa) at a temperature of the order of 20° C., in the presence of potassium hydroxide pellets. This gives 7-(Δ2-imidazolin-2-yl)-5-(pyridin-3-yl)-1H,3H-pyrrolo[1,2-c]thiazole (10.1 g) in the form of beige crystals melting at 188° C.

The methyl 5-(pyridin-3-yl)-1H,3H-pyrrolo[1,2-c]thiazole-7-carbodithioate can be prepared in the following manner:

S-Methyl 5-(pyridin-3-yl)-1H,3H-pyrrolo[1,2-c]thiazole-7-thiocarboximidate hydroiodide (85.3 g) is added to pyridine (950 cc) saturated at a temperature of the order of 15° C. with a gaseous stream of hydrogen sulphide. The suspension obtained is stirred at a temperature of the order of 20° C. for 16 hours and is then poured into distilled water (6,000 cc). The crystals which have appeared are filtered off, washed 6 times with distilled water (1,500 cc in total) and then dissolved in boiling acetonitrile (4,000 cc). The solution obtained is treated with decolourising charcoal (0.5 g) and filtered hot. The filtrate is cooled at a temperature of the order of 4° C. for 16 hours. Th crystals which have appeared are filtered off, washed 3 times with acetonitrile (750 cc in total) and 3 times with diethyl ether (750 cc in total) and then dried under reduced pressure (20 mm Hg; 2.7 kPa) at a temperature of the order of 20° C., in the presence of potassium hydroxide pellets. This gives methyl 5-(pyridin-3-yl)-1H,3H-pyrrolo[1,2-c]thiazole-7-carbodithioate (44.7 g) in the form of orange-yellow crystals melting at 158° C.

The S-methyl 5-(pyridin-3-yl)-1H,3H-pyrrolo[1,2-c]thiazole-7-carboximidate hydroiodide is prepared as in Example 8.

EXAMPLE 27

Phosphoryl chloride (16.4 g) is added in the course of 10 minutes, at a temperature of the order of 10° C., to dimethylformamide (55 cc). The solution obtained is added dropwise in the course of 25 minutes, with stirring, at a temperature of the order of 4° C., to a solution of 5-(pyridin-3-yl)-1H,3H-pyrrolo[1,2-c]thiazole (14.4 g) in dimethylformamide (130 cc). The solution obtained is stirred at a temperature of the order of 20° C. for 16 hours. Crystals appear. A 2N aqueous solution of sodium hydroxide (215 cc) is then added to the suspension obtained; the solution obtained is poured into distilled water (2,150 cc) and extracted 3 times with ethyl acetate (1,800 cc in total). The organic extracts are combined, washed 5 times with distilled water (2,000 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (13.4 g). This product is dissolved in boiling ethanol (120 cc). The solution obtained is cooled at a temperature of the order of 4° C. for 2 hours. The crystals which have appeared are filtered off, washed twice with ethanol cooled to a temperature of the order of 4° C. (20 cc in total) and then 3 times with isopropyl ether (150 cc in total) and dried under reduced pressure (20 mm Hg; 2.7 kPa) at a temperature of the order of 20° C., in the presence of potassium hydroxide pellets. This gives a product (7.4 g) melting at 104° C. This product is combined with the product prepared in the same way in another earlier operation (3 g) and is dissolved in boiling ethanol (60 cc). The solution obtained is treated with decolourising charcoal (0.5 g) and filtered hot. The filtrate is cooled at a temperature of the order of 4° C. for 2 hours. The crystals which have appeared are filtered off, washed 3 times with ethanol cooled to a temperature of the order of 4° C. (15 cc in total) and 3 times with isopropyl ether (75 cc in total) and then dried under reduced pressure (20 mm Hg; 2.7 kPa) at a temperature of the order of 20° C., in the presence of potassium hydroxide pellets. This gives 5-(pyridin-3-yl)-1H,3H-pyrrolol[1,2-c]thiazole-7-carboxaldehyde (7.9 g) in the form of light beige crystals melting at 104° C.

The 5-(pyridin-3-yl)-1H,3H-pyrrolo[1,2-c]thiazole is prepared in the following manner:

A mixture of 5-(pyridin-3-yl)-1H,3H-pyrrolo[1,2-c]thiazole-7-carboxylic acid (36.9 g) and copper powder (1.8 g) is heated at a temperature of the order of 250° C. for 30 minutes. The reaction mixture is cooled to a temperature of the order of 20° C. and is then taken up in methylene chloride (500 cc). The suspension obtained is washed twice with a 2N aqueous solution of sodium hydroxide (200 cc in total) and filtered. The organic phase is decanted and washed 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (25.3 g). This product is chromatographed on a column of diameter 4 cm, containing silica (0.063–0.2 mm) (250 g), elution being carried out with a mixture of cyclohexane and ethyl acetate (50/50 by volume), 600 cc fractions being collected. The first fraction is discarded and the next two are combined and concentrated to dryness under reduced pressure (20 mm Hg; 2.7 kPa) at a temperature of the order of 60° C. This gives 5-(pyridin-3-yl)-1H,3H-pyrrolo[1,2-c]thiazole (21.3 g) in the form of orange crystals melting at 74° C.

The 5-(pyridin-3-yl)-1H,3H-pyrrolo[1,2-c]thiazole-7-carboxylic acid is prepared as in Example 3.

EXAMPLE 28

Methanesulphonic acid (14.4 g) is added to a solution of 5-(pyridin-3-yl)-1H,3H-pyrrolo[1,2-c]thiazole-7-carboxamide (36.8 g) in acetic acid (500 cc). A solution of 85% pure (by weight) 3-chloroperbenzoic acid (67 g) in methylene chloride (1,000 cc) is added dropwise to the solution obtained in the course of 40 minutes, at a temperature of the order of 20° C. The solution obtained is stirred at a temperature of the order of 20° C. for 16 hours and the reaction mixture is then added in the course of 2 hours 30 minutes to a 10N aqueous solution of sodium hydroxide (1,200 cc), the temperature of the reaction mixture being kept at about 20° C. The solid which has appeared is filtered off, washed 4 times with a mixture of chloroform and methanol (80/20 by volume) (4,000 cc in total), 4 times with distilled water (1,000 cc in total) and 3 times with acetone (300 cc in total) and then dried under reduced pressure (20 mm Hg; 2.7 kPa) at a temperature of the order of 20° C., in the presence of potassium hydroxide pellets. This gives a product (24.8 g). The filtrate and the mother liquors from the previous washings are combined; the organic phase is decanted, dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a product (17.6 g). This product is suspended in distilled water (150 cc) and the crystals are filtered off, washed 3 times with distilled water (75 cc in total) and 3 times with acetone (75 cc in total) and then dried under reduced pressure (20 mm Hg; 2.7 kPa) at a temperature of the order of 20° C., in the presence of potassium hydroxide pellets. The product thus obtained (3.3 g) is combined with the previously isolated product (24.8 g) and is dissolved in a boiling 2N aqueous solution of acetic acid (1,000 cc). The solution obtained is treated with decolourising charcoal (0.5 g) and filtered hot. The filtrate is cooled at a temperature of the order of 4° C. for 3 hours. The crystals which have appeared are filtered off, washed twice with a 2N aqueous solution of acetic acid (100 cc in total), 3 times with distilled water (300 cc in total), 3 times with ethanol (150 cc in total) and 3 times with diethyl ether (150 cc in total) and then dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carboxamide 2,2-dioxide (17 g) in the form of pale yellow crystals melting at 264° C.

The 5-(pyridin-3-yl)-1H,3H-pyrrolo[1,2-c]thiazole-7-carboxamide can be prepared as described in Example 1.

EXAMPLE 29

A solution of ethyl 6-{[5-(pyridin-3-yl)-1H,3H-pyrrolo[1,2-c]thiazol-7-yl]-carbonylamino}-hexanoate (2.9 g) in a mixture of a 2N aqueous solution of sodium hydroxide (7.5 cc) and ethanol (30 cc) is stirred at a temperature of the order of 20° C. for 16 hours. The solution is then concentrated to dryness under reduced pressure (20 mm Hg; 2.7 kPa) at a temperature of the order of 60° C. The residue obtained is dissolved in water (50 cc) and the solution obtained is brought to a pH of the order of 3 by adding a 0.5N aqueous solution of hydrochloric acid (40 cc). The crystals which have appeared are filtered off, washed 5 times with distilled water (150 cc in total), 3 times with acetone (45 cc in total) and then twice with diethyl ether (30 cc in total) and dried under reduced pressure (20 mm Hg; 2.7 kPa) at a temperature of the order of 20° C., in the presence of potassium hydroxide pellets. This gives a crude product (2 g) melting at 152° C. This product is dissolved in boiling ethanol (40 cc). The solution obtained is treated with decolourising charcoal (0.5 g) and filtered hot. The filtrate is cooled at a temperature of the order of 4° C. for 3 hours. The crystals which have appeared are filtered off, washed twice with ethanol (10 cc in total) and then 3 times with diethyl ether (30 cc in total) and dried under reduced pressure (20 mm Hg; 2.7 kPa) at a temperature of the order of 20° C., in the presence of potassium hydroxide pellets. This gives 6-{[5-(pyridin-3-yl)-1H,3H-pyrrolo[1,2-c]thiazol-7-yl]-carbonylamino}-hexanoic acid (1.5 g) in the form of cream crystals melting at 158° C.

The ethyl 6-{[5-(pyridin-3-yl)-1H,3H-pyrrolo[1,2-c]thiazol-7-yl]-carbonylamino}-hexanoate is prepared in the following manner:

A solution of ethyl 6-aminohexanoate (4.1 g) and triethylamine (5.3 g) in methylene chloride (45 cc) is added in the course of 10 minutes, at a temperature of between 22° C. and 32° C., to a suspension of 7-chloroformyl-5-(pyridin-3-yl)-1H,3H-pyrrolo[1,2-c]thiazole hydrochloride (7.8 g) in methylene chloride (130 cc). The solution obtained is stirred at a temperature of the order of 20° C. for 16 hours and is then diluted with methylene chloride (150 cc), washed 4 times with distilled water (800 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (9.3 g). This product is chromatographed on a column of diameter 3 cm, containing silica (0.063-0.2 mm) (100 g), elution being carried out with mixtures of ethylene chloride and ethanol and 300 cc fractions being collected. The first three fractions from elution with pure methylene chloride and the next 2 fractions from elution with a mixture of methylene chloride and methanol (98/2 by volume) are discarded and the next 2 fractions from elution with a mixture of methylene chloride and methanol (98/2 by volume) and the next fraction from elution with a mixture of methylene chloride and methanol (96/4 by volume) are combined and concentrated to dryness under reduced pressure (20 mm Hg; 2.7 kPa) at a temperature of the order of 60° C. This gives ethyl 6-{[5-(pyridin-3-yl)-1H,3H-pyrrolo[1,2-c]thiazol-7-yl]carbonylamino)-hexanoate (2.9 g) in the form of a brown oil.

[Rf=0.55; chromatography on a thin layer of silica gel; solvent: methylene chloride/methanol (90/10 by volume)].

The ethyl 6aminohexanoate can be prepared according to C. S. MARVEL, J. R. ELLIOTT, F. E. BOETTNER and H. YUSKA, J. Amer. Chem. Soc., 68, 1681 (1946).

EXAMPLE 30

A suspension of 3-(pyridin-3-yl)-5,6,7,8-tetrahydroindolizine-1-carbonitrile (5.2 g) and powdered potassium hydroxide (7.7 g) in tert.-butyl alcohol (120 cc) is heated for 13 hours at a temperature on the order of 80° C. The suspension is then concentrated to dryness under reduced pressure (20 mm Hg; 2.7 kPa) at a temperature of the order of 60° C. The residue is taken up in distilled water (200 cc) and the suspension obtained is stirred at a temperature of the order of 20° C. for 1 hour. The crystals which have appeared are filtered off, washed 5 times with distilled water (250 cc in total) and dried under reduced pressure (20 mm Hg; 2.7 kPa) at a temperature of the order of 20° C., in the presence of potassium hydroxide pellets. This gives a crude product (4.1 g) melting at 180° C. This product, combined with the product prepared in the same way in another operation (1.1 g), is dissolved in boiling acetonitrile (160 cc). The turbid solution obtained is treated with decolourising charcoal (0.5 g) and filtered hot. The filtrate is cooled at a temperature of the order of 4′ C. for 2 hours. The crystals which have appeared are filtered off, washed 3 times with acetonitrile (75 cc in total) and 3 times with isopropyl ether (75 cc in total) and then dried under reduced pressure (20 mm Hg; 2.7 kPa) at a temperature of the order of 20° C., in the presence of potassium hydroxide pellets. This gives 3-(pyridin-3-yl)-5,6,7,8-tetrahydroindolizine-1-carboxamide (4 g) in the form of light beige crystals melting at 184° C.

The 3-pyridin-3-yl)-5,6,7,8-tetrahydroindolizine-1-carbonitrile can be prepared in the following manner:

A suspension of N-nicotinoylpiperidine-2-carboxylic acid (14.7 g) in a mixture of 2-chloroacrylonitrile (50 cc) and acetic anhydride (65 cc) is heated at a temperature of the order of 90° C. for 4 hours. After stirring for 16 hours at a temperature of the order of 20° C., the crystals are filtered off, washed 3 times with acetic anhydride (75 cc in total) and dried under reduced pressure (20 mm Hg; 2.7 kPa) at a temperature of the order of 20° C., in the presence of potassium hydroxide pellets. The product thus obtained (10 g) is dissolved in distilled water (100 cc). After the addition of a 10N aqueous solution of sodium hydroxide (50 cc) at a temperature of the order of 10° C., a suspension is obtained, which is stirred at a temperature of the order of 20° C. for 1 hour and then extracted 3 times with ethyl acetate (450 cc in total). The organic extracts are combined, washed 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a product (8.8 g), which is chromatographed on a column of diameter 6 cm, containing silica (0.04–0.063 mm) (480 g), elution being carried out with ethyl acetate under a pressure of 0.5 bar (51 kPa) and 100 cc fractions being collected. The first 14 fractions are discarded and the next 6 fractions are combined and concentrated to dryness under reduced pressure (20 mm Hg; 2.7 kPa) at a temperature of the order of 60° C. This gives 3-(pyridin-3-yl)-5,6,7,8-tetrahydroindolizine-1-carbonitrile (5.2 g) in the form of brown crystals melting at 112° C.

The N-nicotinoylpiperidine-2-carboxylic acid can be prepared in the following manner:

A solution of ethyl N-nicotinoylpiperidine-2-carboxylate (34.1 g) in a mixture of a 2N aqueous solution of sodium hydroxide (130 cc) and ethanol (325 cc) is stirred at a temperature of the order of 20° C. for 16 hours. The solvent is then evaporated off under reduced pressure (20 mm Hg; 2.7 kPa) at a temperature of the order of 60° C. The residue obtained is dissolved in distilled water (250 cc). The turbid solution obtained is treated with decolourising charcoal (0.5 g) and filtered. The filtrate, kept at a temperature of 20° C., is brought to a pH of the order of 3 by adding a 4N aqueous solution of hydrochloric acid (80 cc). The suspension obtained is stirred at a temperature of the order of 20° C. for 1 hour and the crystals are filtered off, washed 4 times with distilled water (200 cc in total), 3 times with acetone (150 cc in total) and once with diethyl ether (50 cc) and then dried under reduced pressure (20 mm Hg; 2.7 kPa) at a temperature of the order of 20° C., in the presence of potassium hydroxide pellets. This gives N-nicotinoylpiperidine-2-carboxylic acid (14.8 g) in the form of white crystals melting at 194° C.

The ethyl N-nicotinoylpiperidine-2-carboxylate can be prepared in the following manner:

Triethylamine (182 g) is initially added, at a temperature of between 20° C. and 31° C., to a solution of ethyl piperidine-2-carboxylate (72.9 g) in chloroform (1,120 cc), this being followed, in the course of 35 minutes, at a temperature of between 26° C. and 50° C., by nicotinoyl chloride hydrochloride (160.2 g). The suspension obtained is stirred at a temperature of the order of 20° C. for 16 hours and then washed 5 times with distilled water (1,500 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (174 g), which is chromatographed on a column of diameter 8 cm, containing silica (0.063–0.2 mm) (1,740 g), elution being carried out with mixtures of cyclohexane and ethyl acetate and 1,000 cc fractions being collected. The first 5 fractions from elution with a mixture of cyclohexane and ethyl acetate (80/20 by volume), the next 5 fractions from elution with a mixture of cyclohexane and ethyl acetate (70/30 by volume), the next 7 fractions from elution with a mixture of cyclohexane and ethyl acetate (60/40 by volume) and the next fraction from elution with a mixture of cyclohexane and ethyl acetate (50/50 by volume) are discarded. The next 8 fractions from elution with a mixture of cyclohexane and ethyl acetate (50/50 by volume) and the next 7 fractions from elution with pure ethyl acetate are combined and concentrated to dryness under reduced pressure (20 mm Hg; 2.7 kPa) at a temperature of the order of 60° C. This gives ethyl N-nicotinoylpiperidine-2-carboxylate (99.3 g) in the form of an orange oil.

($R_f$=0.46; chromatography on a thin layer of silica gel; eluent: ethyl acetate).

The present invention also provides pharmaceutical compositions comprising a compound of the formula (I), in the free form or in the form of an addition salt with a pharmaceutically acceptable acid or base, and a compatible pharmaceutical carrier (which may be a coating). The said carrier is normally inert but may be, or contain, a physiologically active ingredient. The compositions of the invention can be made up in a form suitable for oral, parenteral, rectal or topical administration.

Tablets, pills, powders (in particular in gelatine capsules or in cachets) and granules are examples of solid compositions for oral administration. In these compositions, the active compound of the invention may be mixed with one or more inert diluents such as starch, cellulose, sucrose, lactose or silica. These compositions can also comprise carriers other than diluents, e.g. one or more adjuvants, including lubricants such as magnesium stearate or talc, a colorant, a coating (coated tablets) or a lacquer.

Solutions, suspensions, emulsions, syrups and pharmaceutically acceptable elixirs containing inert diluents such as water, ethanol, glycerol, vegetable oils or paraffin oil are examples of liquid compositions for oral administration. These compositions can comprise substances in addition to diluents, e.g. wetting, sweetening, thickening, flavouring or stabilising agents.

Sterile compositions for parenteral administration are preferably suspensions, emulsions or aqueous or nonaqueous solutions. Water, propylene glycol, a polyethylene glycol, vegetable oils, in particular olive oil, injectable organic esters, e.g. ethyl oleate, or other suitable organic solvents can be employed as the solvent or vehicle. These compositions can also contain adjuvants, in particular wetting agents, agents for imparting isotonicity, emulsifiers, dispersing agents and stabilisers. Sterilisation can be carried out in several ways, e.g. by filtration under aseptic conditions, by incorporating sterilising agents into the composition, by irradiation or by heating. The compositions can also be prepared in the form of sterile solid compositions which are dissolved in an injectable sterile medium at the time of use.

Compositions for rectal administration are suppositories or rectal capsules, which contain, in addition to the active compound, excipients such as cocoa butter, semi-synthetic glycerides or polyethylene glycols.

Compositions for topical administration can be, e.g. creams, ointments, lotions, eye lotions, mouthwashes, nose drops or aerosols.

In human therapy, the compounds of the invention are particularly useful in the prophylactic and therapeutic treatment of thrombotic complaints. The doses depend on the desired effect and the duration of the treatment. For an adult, a dosage of generally between 100 and 1,000 mg per day, administered orally in one or more individual doses, or of between 10 and 100 mg, administered parenterally in one or more injections, is generally suitable.

The physician will determine the dosage which he considers to be most appropriate as a function of the age, the weight and all the other factors peculiar to the patient to be treated.

The Examples which follow illustrate compositions according to the invention.

EXAMPLE A

Tablets containing 200 mg doses of active ingredient and having the following composition are prepared by the usual technique:

5-(pyridin-3-yl)-1H,3H-pyrrolo[1,2-c]thiazole-7-carboxamide—200 mg
starch—60 mg
lactose—50 mg
magnesium stearate—2 mg

EXAMPLE B

An injectable solution containing 20 mg of active product and having the following composition is prepared:

6-(pyridin-3-yl)-1,2-dihydro-4H-pyrrolo[1,2-c]-1,3-thiazine-8-carboxamide—20 mg
0.1N methanesulphonic acid—0.77 cc
injectable solution q.s—2 cc

We claim:

1. A heterocyclic compound of the formula:

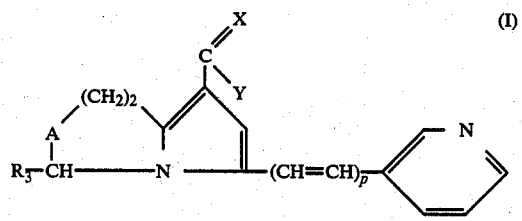

in which A represents —S—, —SO— or SO$_2$—, R$_3$ represents hydrogen, alkyl or phenyl unsubstituted or substituted by halogen, alkyl, alkoxy or trifluoromethyl, and (a) X represents oxygen, sulphur, imino or hydroxyimino, p represents 0 or 1 and Y represents a radical of the formula:

in which R$_1$ and R$_2$ both represent hydrogen, or R$_1$ represents hydrogen and R$_2$ represents hydroxyl or alkyl of 1 to 5 carbon atoms, which is substituted by a carboxyl, amino, alkylamino, dialkylamino, hydroxyalkylamino, morpholino or imidazolyl, or piperazin-1-yl radical (unsubstituted or substituted in the 4-position by alkyl, benzyl optionally substituted by halogen, alkyl, alkoxy or trifluoromethyl, or phenyl optionally substituted by halogen, alkyl, alkoxy or trifluoromethyl) or a piperidino or pyrrolidin-1-yl radical, or R$_2$ represents phenyl substituted by one or more hydroxyl, carboxyl, amino, alkylamino or dialkylamino radicals, or R$_1$ and R$_2$ form, with the nitrogen atom to which they are bonded, a 5-membered or 6-membered ring which can also contain another heteroatom selected from oxygen, sulphur and nitrogen and which is unsubstituted or substituted by alkyl, alkoxycarbonyl, hydroxyalkyl, aminoalkyl, alkylaminoalkyl or dialkylaminoalkyl, a benzyl radical (optionally substituted by a halogen atom or an alkyl, alkoxy or trifluoromethyl radical) or a pyrrolidin-1-yl carbonylalkyl radical, or (b) X represents dialkylhydrazono, Y represents amino and p represents 0 or 1, or (c) X and Y form with the carbon atom to which they are bonded, a Δ2-thiazolin-2-yl or Δ2-imidazolin-2-yl radical and p represents 0 or 1, or (d) X represents oxygen, Y represents hydrogen and p is 0, the said alkyl radicals and alkyl portions being straight-chain or branched-chain and, unless stated otherwise, containing 1 to 4 carbon atoms each, and the tautomeric forms of the compounds where X represents imino, hydroxyimino or dialkylhydrazono and Y represents a radical of the formula (II) in which R$_1$ represents a hydrogen atom, or where X represents oxygen or sulphur and Y represents a radical of the general formula (II) in which R$_1$ represents hydrogen and R$_2$ represents hydroxyl; and its addition salts with acids and, where they exist, its metal salts and its addition salts with nitrogen-containing bases.

2. A heterocyclic compound according to claim 1 in which A is —S—, —SO$_2$—, R$_3$ is hydrogen, X is oxygen, sulphur, imino, or hydroxyimino, p is 0 or 1 and Y is a radical of formula:

in which R$_1$ and R$_2$ are both hydrogen or R$_1$ is hydrogen and R$_2$ is hydroxy or dialkylaminoethyl, or R$_1$ and R$_2$ together with the nitrogen atom to which they are attached represent a saturated six-membered ring which may contain a second hetero-atom chosen from oxygen and nitrogen and which is unsubstituted or substituted by alkyl or benzyl, or X represents dialkylhydrazono, Y is amino, and p is 0, or the radical —C(:X)Y is Δ2-thiazolin-2-yl or —CHO and p is 0.

3. A heterocyclic compound according to claim 1, in which A is —S—, or $SO_2$—, $R_3$ is hydrogen, p is 0, X is oxygen, sulphur, or hydroxymino, and Y is amino, piperazin-1-yl, or 4-methyl-piperazin-1-yl, or X is dialkylhydrazono, and Y is amino.

4. A compound according to claim 1 which is 6-(pyridin-3-yl)-1,2-dihydro-4H-pyrrolo[1,2-c]-1,3-thiazine-8-carboxamide and its pharmaceutically acceptable salts.

5. A method for the prophylactic or therapeutic treatment of thrombosis which comprises administering to a subject in need of such treatment an effective amount of a compound according to claim 1 in the free form or in the form of an addition salt with a pharmaceutically acceptable acid or base.

6. A pharmaceutical composition useful for the prophylactic or therapeutic treatment of thrombosis comprising an effective amount of at least one compound according to claim 1, in the free form or in the form of an addition salt with a pharmaceutically acceptable acid or base, in association with one or more compatible pharmaceutically acceptable carriers.

* * * * *